US007736319B2

(12) United States Patent
Patangay et al.

(10) Patent No.: US 7,736,319 B2
(45) Date of Patent: Jun. 15, 2010

(54) ISCHEMIA DETECTION USING HEART SOUND TIMING

(75) Inventors: Abhilash Patangay, Little Canada, MN (US); Yi Zhang, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 501 days.

(21) Appl. No.: 11/625,003

(22) Filed: Jan. 19, 2007

(65) Prior Publication Data

US 2008/0177191 A1 Jul. 24, 2008

(51) Int. Cl.
*A61B 5/02* (2006.01)

(52) U.S. Cl. ..................................................... 600/528
(58) Field of Classification Search ................. 600/514, 600/528
See application file for complete search history.

(56) References Cited

U.S. PATENT DOCUMENTS

| | | |
|---|---|---|
| 3,799,147 A | 3/1974 | Adolph et al. |
| 4,094,308 A | 6/1978 | Cormier |
| 4,220,160 A | 9/1980 | Kimball et al. |
| 4,289,141 A | 9/1981 | Cormier |
| 4,428,378 A | 1/1984 | Anderson et al. |
| 4,428,380 A | 1/1984 | Wong et al. |
| 4,446,872 A | 5/1984 | Marsoner et al. |
| 4,548,204 A | 10/1985 | Groch et al. |
| 4,628,939 A | 12/1986 | Little et al. |
| 4,649,930 A | 3/1987 | Groch et al. |
| 4,702,253 A | 10/1987 | Nappholz et al. |
| 4,763,646 A | 8/1988 | Lekholm |
| 4,773,401 A | 9/1988 | Citak et al. |
| 4,796,639 A | 1/1989 | Snow et al. |
| 4,905,706 A | 3/1990 | Duff et al. |
| 4,915,113 A | 4/1990 | Holman |
| 4,967,760 A | 11/1990 | Bennett et al. |
| 4,981,139 A | 1/1991 | Pfohl |
| 4,989,611 A | 2/1991 | Zanetti et al. |
| 5,007,427 A | 4/1991 | Suzuki et al. |

(Continued)

FOREIGN PATENT DOCUMENTS

EP          0709058 A1    5/1996

(Continued)

OTHER PUBLICATIONS

"U.S. Appl. No. 11/148,107, Final Office Action mailed Jan. 14, 2009", 10 pgs.

(Continued)

*Primary Examiner*—Mark W Bockelman
*Assistant Examiner*—Eric D. Bertram
(74) *Attorney, Agent, or Firm*—Schwegman, Lundberg & Woessner, P.A.

(57) ABSTRACT

A system comprising a heart sound sensor to produce a heart sound signal representative of at least one heart sound. A signal analyzer circuit measures a baseline time interval between a first detected physiologic cardiovascular event and at least one second detected physiologic cardiovascular event. At least one of the first and second detected physiologic cardiovascular events includes a heart sound event obtained from the heart sound signal. The sensor analyzer circuit determines that an ischemic event occurred at least in part by detecting a specified measured subsequent change from the established baseline time interval. Other systems and methods are disclosed.

36 Claims, 10 Drawing Sheets

U.S. PATENT DOCUMENTS

| | | |
|---|---|---|
| 5,010,889 A | 4/1991 | Bredesen et al. |
| 5,012,815 A | 5/1991 | Bennett, Jr. et al. |
| 5,025,809 A | 6/1991 | Johnson et al. |
| 5,072,458 A | 12/1991 | Suzuki |
| 5,111,818 A | 5/1992 | Suzuki et al. |
| 5,137,019 A | 8/1992 | Pederson et al. |
| 5,159,932 A | 11/1992 | Zanetti et al. |
| 5,199,428 A | 4/1993 | Obel et al. |
| 5,218,969 A | 6/1993 | Bredesen et al. |
| 5,301,679 A | 4/1994 | Taylor |
| 5,337,752 A | 8/1994 | Reeves |
| 5,365,932 A | 11/1994 | Greenhut |
| 5,472,453 A | 12/1995 | Alt |
| 5,496,361 A | 3/1996 | Moberg et al. |
| 5,554,177 A | 9/1996 | Kieval et al. |
| 5,593,431 A | 1/1997 | Sheldon |
| 5,628,777 A | 5/1997 | Moberg et al. |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,725,562 A | 3/1998 | Sheldon |
| 5,792,195 A | 8/1998 | Carlson et al. |
| 5,836,987 A | 11/1998 | Baumann et al. |
| 5,860,933 A | 1/1999 | Don Michael |
| 5,935,081 A | 8/1999 | Kadhiresan |
| 5,987,352 A | 11/1999 | Klein et al. |
| 5,991,661 A | 11/1999 | Park et al. |
| 6,002,777 A | 12/1999 | Grasfield et al. |
| 6,009,349 A | 12/1999 | Mouchawar et al. |
| 6,021,350 A | 2/2000 | Mathson |
| 6,026,324 A | 2/2000 | Carlson |
| 6,044,297 A | 3/2000 | Sheldon et al. |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,076,015 A | 6/2000 | Hartley et al. |
| 6,077,227 A | 6/2000 | Miesel |
| 6,104,949 A | 8/2000 | Pitts Crick et al. |
| 6,115,628 A | 9/2000 | Stadler et al. |
| 6,115,630 A | 9/2000 | Stadler et al. |
| 6,144,880 A | 11/2000 | Ding et al. |
| 6,152,884 A | 11/2000 | Bjorgaas |
| 6,193,668 B1 | 2/2001 | Chassaing et al. |
| 6,208,900 B1 | 3/2001 | Ecker et al. |
| 6,223,082 B1 | 4/2001 | Bakels et al. |
| 6,230,059 B1 | 5/2001 | Duffin |
| 6,236,882 B1 | 5/2001 | Lee et al. |
| 6,251,126 B1 | 6/2001 | Ottenhoff et al. |
| 6,264,611 B1 | 7/2001 | Ishikawa et al. |
| 6,269,269 B1 | 7/2001 | Ottenhoff et al. |
| 6,272,377 B1 | 8/2001 | Sweeney et al. |
| 6,272,379 B1 | 8/2001 | Fischell et al. |
| 6,273,856 B1 | 8/2001 | Sun et al. |
| 6,298,269 B1 | 10/2001 | Sweeney |
| 6,312,378 B1 | 11/2001 | Bardy |
| 6,314,323 B1 | 11/2001 | Ekwall et al. |
| 6,324,421 B1 | 11/2001 | Stadler et al. |
| 6,347,245 B1 | 2/2002 | Lee et al. |
| 6,351,672 B1 | 2/2002 | Park et al. |
| 6,351,673 B1 | 2/2002 | Ding et al. |
| 6,360,127 B1 | 3/2002 | Ding et al. |
| 6,366,811 B1 | 4/2002 | Carlson |
| 6,368,283 B1 | 4/2002 | Xu et al. |
| 6,381,493 B1 | 4/2002 | Stadler et al. |
| 6,397,100 B2 | 5/2002 | Stadler et al. |
| 6,409,675 B1 | 6/2002 | Turcott |
| 6,415,033 B1 | 7/2002 | Halleck et al. |
| 6,440,082 B1 | 8/2002 | Joo et al. |
| 6,459,929 B1 | 10/2002 | Hopper et al. |
| 6,466,821 B1 | 10/2002 | Pianca et al. |
| 6,477,406 B1 | 11/2002 | Turcott |
| 6,478,746 B2 | 11/2002 | Chassaing et al. |
| 6,480,733 B1 | 11/2002 | Turcott |
| 6,491,639 B1 | 12/2002 | Turcott |
| 6,496,715 B1 | 12/2002 | Lee et al. |
| 6,496,721 B1 | 12/2002 | Yonce |
| 6,501,983 B1 | 12/2002 | Natarajan et al. |
| 6,520,924 B2 | 2/2003 | Lee |
| 6,527,729 B1 | 3/2003 | Turcott |
| 6,531,907 B2 | 3/2003 | Dooley et al. |
| 6,542,775 B2 | 4/2003 | Ding et al. |
| 6,567,700 B1 | 5/2003 | Turcott et al. |
| 6,575,916 B2 | 6/2003 | Halleck et al. |
| 6,625,493 B2 | 9/2003 | Kroll et al. |
| 6,626,842 B2 | 9/2003 | Oka |
| 6,643,548 B1 | 11/2003 | Mai et al. |
| 6,650,940 B1 | 11/2003 | Zhu et al. |
| 6,658,292 B2 | 12/2003 | Kroll et al. |
| 6,665,564 B2 | 12/2003 | Lincoln et al. |
| 6,684,103 B2 | 1/2004 | Ding et al. |
| 6,719,701 B2 | 4/2004 | Lade |
| 6,733,464 B2 | 5/2004 | Olbrich et al. |
| 6,752,765 B1 | 6/2004 | Jensen et al. |
| 6,792,308 B2 | 9/2004 | Corbucci |
| 6,795,732 B2 | 9/2004 | Stadler et al. |
| 6,810,284 B1 | 10/2004 | Bradley |
| 6,810,287 B2 | 10/2004 | Zhu et al. |
| 6,824,519 B2 | 11/2004 | Narimatsu et al. |
| 6,827,690 B2 | 12/2004 | Bardy |
| 6,830,548 B2 | 12/2004 | Bonnet et al. |
| 6,845,263 B2 | 1/2005 | Kawaguchi |
| 6,865,420 B1 | 3/2005 | Kroll |
| 6,913,577 B2 | 7/2005 | Bardy |
| 6,963,777 B2 | 11/2005 | Lincoln et al. |
| 7,010,342 B2 | 3/2006 | Galen et al. |
| 7,065,397 B2 | 6/2006 | Galen et al. |
| 7,072,708 B1 | 7/2006 | Andresen et al. |
| 7,074,195 B2 | 7/2006 | Nelson et al. |
| 7,110,804 B2 | 9/2006 | Baumer et al. |
| 7,110,817 B2 | 9/2006 | Yu et al. |
| 7,113,825 B2 | 9/2006 | Pastore et al. |
| 7,115,096 B2 | 10/2006 | Siejko et al. |
| 7,123,962 B2 | 10/2006 | Siejko et al. |
| 7,139,609 B1 | 11/2006 | Min et al. |
| 7,158,830 B2 | 1/2007 | Yu et al. |
| 7,248,923 B2 | 7/2007 | Maile et al. |
| 7,479,112 B2 | 1/2009 | Sweeney et al. |
| 7,559,901 B2 | 7/2009 | Maile et al. |
| 2002/0001390 A1 | 1/2002 | Kawaguchi |
| 2002/0016548 A1 | 2/2002 | Stadler et al. |
| 2002/0019586 A1 | 2/2002 | Teller et al. |
| 2002/0026122 A1 | 2/2002 | Lee et al. |
| 2002/0035337 A1 | 3/2002 | Oka |
| 2002/0072777 A1 | 6/2002 | Lu |
| 2002/0082645 A1 | 6/2002 | Sweeney |
| 2002/0107450 A1 | 8/2002 | Ogura |
| 2002/0128563 A1 | 9/2002 | Carlson et al. |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0004549 A1 | 1/2003 | Hill et al. |
| 2003/0013974 A1 | 1/2003 | Natarajan et al. |
| 2003/0014083 A1 | 1/2003 | Kupper |
| 2003/0040676 A1 | 2/2003 | Prentice et al. |
| 2003/0045805 A1 | 3/2003 | Sheldon et al. |
| 2003/0045908 A1 | 3/2003 | Condie et al. |
| 2003/0055352 A1 | 3/2003 | Hayek et al. |
| 2003/0055461 A1 | 3/2003 | Girouard et al. |
| 2003/0060854 A1 | 3/2003 | Zhu |

| | | |
|---|---|---|
| 2003/0069608 A1 | 4/2003 | Sweeney |
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0120159 A1 | 6/2003 | Mohler |
| 2003/0125774 A1 | 7/2003 | Salo |
| 2003/0139778 A1 | 7/2003 | Fischell et al. |
| 2003/0158492 A1 | 8/2003 | Sheldon et al. |
| 2003/0158584 A1 | 8/2003 | Cates et al. |
| 2003/0176896 A1 | 9/2003 | Lincoln et al. |
| 2003/0191503 A1 | 10/2003 | Zhu et al. |
| 2003/0208240 A1 | 11/2003 | Pastore et al. |
| 2003/0216620 A1 | 11/2003 | Jain et al. |
| 2003/0229289 A1 | 12/2003 | Mohler et al. |
| 2003/0233130 A1 | 12/2003 | Padmanabhan et al. |
| 2003/0233132 A1 | 12/2003 | Pastore et al. |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0073093 A1 | 4/2004 | Hatlestad |
| 2004/0078059 A1 | 4/2004 | Ding et al. |
| 2004/0078060 A1 | 4/2004 | Ding et al. |
| 2004/0102712 A1 | 5/2004 | Belalcazar et al. |
| 2004/0106960 A1 | 6/2004 | Siejko et al. |
| 2004/0106961 A1 | 6/2004 | Siejko et al. |
| 2004/0106962 A1 | 6/2004 | Mai et al. |
| 2004/0111040 A1 | 6/2004 | Ni et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0004476 A1 | 1/2005 | Payvar et al. |
| 2005/0027323 A1 | 2/2005 | Mulligan et al. |
| 2005/0033190 A1 | 2/2005 | Bauer |
| 2005/0038345 A1 | 2/2005 | Gorgenberg et al. |
| 2005/0060001 A1 | 3/2005 | Singhal et al. |
| 2005/0065448 A1 | 3/2005 | Stahmann et al. |
| 2005/0090870 A1 | 4/2005 | Hine et al. |
| 2005/0102001 A1 | 5/2005 | Maile et al. |
| 2005/0137631 A1 | 6/2005 | Yu et al. |
| 2005/0148896 A1 | 7/2005 | Siejko et al. |
| 2005/0148897 A1 | 7/2005 | Cho et al. |
| 2005/0197674 A1 | 9/2005 | McCabe et al. |
| 2005/0203579 A1 | 9/2005 | Sowelam et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0106322 A1* | 5/2006 | Arand et al. ............ 600/514 |
| 2006/0116593 A1 | 6/2006 | Zhang et al. |
| 2006/0161070 A1 | 7/2006 | Siejko et al. |
| 2006/0259087 A1 | 11/2006 | Baynham et al. |
| 2006/0270939 A1 | 11/2006 | Wariar et al. |
| 2006/0282000 A1* | 12/2006 | Zhang et al. ............ 600/528 |
| 2006/0287684 A1 | 12/2006 | Baynham et al. |
| 2007/0043393 A1 | 2/2007 | Brockway et al. |
| 2007/0054871 A1 | 3/2007 | Pastore et al. |
| 2007/0150005 A1 | 6/2007 | Sih et al. |
| 2007/0150015 A1 | 6/2007 | Zhang et al. |
| 2007/0276453 A1 | 11/2007 | Hill et al. |
| 2007/0299356 A1 | 12/2007 | Wariar et al. |
| 2008/0015652 A1 | 1/2008 | Maile et al. |
| 2008/0081354 A1 | 4/2008 | Qu et al. |

FOREIGN PATENT DOCUMENTS

| | | |
|---|---|---|
| EP | 1179317 A2 | 2/2002 |
| EP | 1247485 A1 | 10/2002 |
| JP | 2000-316825 | 11/2000 |
| WO | WO-01/24876 A1 | 4/2001 |
| WO | WO-0156651 A1 | 8/2001 |
| WO | WO-0167948 A2 | 9/2001 |
| WO | WO-03041797 A2 | 5/2003 |
| WO | WO-2004012815 A1 | 2/2004 |
| WO | WO-2004050178 A1 | 6/2004 |
| WO | WO-2004/060483 A1 | 7/2004 |
| WO | WO-2005122902 A1 | 12/2005 |
| WO | WO-2006028575 A2 | 3/2006 |
| WO | WO-2006028575 A3 | 3/2006 |
| WO | WO-2006041337 A1 | 4/2006 |
| WO | WO-2006078757 A1 | 7/2006 |
| WO | WO-2006127594 A2 | 11/2006 |

OTHER PUBLICATIONS

"U.S. Appl. No. 11/148,107, Response filed Oct. 20, 2008 to Non-Final Office Action mailed Jul. 18, 2008", 9 pgs.

"U.S. Appl. No. 11/148,107, Non-Final Office Action mailed Jul. 18, 2008", 8 pgs.

Abrams, Jonathan, "Current Concepts of the Genesis of Heart Sounds", *JAMA* 239(26), (Jun. 30, 1978).

Amende, I., "Hemodynamics in ischemia: diastolic phase", *Z. Kardiol.*, 73 Suppl 2, [Article in German], (1984), 127-33.

Bulgrin, J. R., et al., "Comparison of Short-Time Fourier, Wavelet and Time-Domain Analyses of Intracardiac Sounds", *Biomedical Sciences Instrumentation*, 29, (1993), 465-472.

Carlson, Gerrard M., et al., "Hemodynamic Stability Assessment Based on Heart Sounds", U.S. Appl. No. 11/277,773, filed Mar. 29, 2006, 39 Pages.

Collins, Sean, "Diagnostic Utility of an S3 in Dyspneic ED Patients", *Inovise Medical Inc, University of Cincinnati Medical Center*, (2005), 6 Pages.

Dzwonczyk, R., et al., "Myocardial electrical impedance responds to ischemia and reperfusion in humans", *IEEE Transactions on Biomedical Engineering*, 51(12), (Dec. 2004), 2206-2209.

Hada, Yoshiyuki, et al., "Pulsus alternans determined by biventricular simultaneous systolic time intervals", *Circulation*, 65(3), (Mar. 1982), 617-26.

Haro, Carlos, et al., "Respiration-Synchronized Heart Sound Trending", U.S. Appl. No. 11/561,428, filed Nov. 20, 2006, 54 Pages.

Ji, J., "An Ultraminiature CMOS Pressure Sensor for a Multiplexed Cardiovascular Catheter", *IEEE Transactions on Electron Devices*, vol. 39, No. 10, (Oct. 1992), pp. 2260-2267.

Kameli, Nader, "Integrated System for Managing Patients With Heart Failure", U.S. Appl. No. 11/553,103, filed Oct. 26, 2006, 41 Pages.

Krayenbuhl, H. P., "Hemodynamics in ischemia. Systolic phase", *Z. Kardiol.*, 73 Suppl 2, [Article in German], (1984), 119-25.

Leatham, A., "Splitting of the First and Second Heart Sounds", *Lancet*, 267 (6839), (Sep. 25, 1954), 607-614.

Leonelli, Fabio M., et al., "Systolic and Diastolic Effects of Variable Atroventricular Delay and Patients with Complete Hear Block and Normal Ventricular Function", *Amer. J-Cardiology*, vol. 80, pp. 294-298, (Aug. 1, 1997), 294-298.

Makhoul, John, "Linear Prediction: A Tutorial Review", *Proceedings of the IEEE*, 63, (Apr. 1975), 561-580.

Marcus, G. M., et al., "Association Between Phonocardiographic Third and Fourth Heart Sounds and Objective Measures of Left Ventricular Function", *JAMA*, 293(18), (May 11, 2005), 2238-44.

Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technnological Challenges of the 1990s, (1992), 856-862.

Palomo, A. R., et al., "Echo-phonocardiographics determination of left atrial and left ventrical filling pressures with and without mitral stenosis", *Circulation*, vol. 61, No. 5, (May 1980), 1043-1047.

Panju, Akbar A., et al., "Is This Patient Having a Myocardial Infraction?", *JAMA*, 280(14), (Oct. 14, 1998), 1256-1263.

Ritter, P., et al., "A Built-In System Based on the Peak Endocardial Acceleration (PEA) for AV-Delay Optimization in DDDR Pacing", *PACE*, 20(5) (Part II), Abstract of Paper presented at Europace '97, (May 1997), 1567.

Ritter, P., et al., "New Method for Determining the Optimal Atrio-Ventricular Delay in Patients Place in DDD Mode for Complete Atrio-Ventricular Block", *NASPE abstract #237*, p. 885, (1995), 3.

Salerno, D. M., "Seismocardiography for monitoring changes in left ventricular function during ischemia.", *Chest*, 100(4), (Oct. 1991), 991-3.

Siejko, Krzysztof Z., et al., "A Third Heart Sound Activity Index for Heart Failure Monitoring", U.S. Appl. No.11/465 878, filed Aug. 21, 2006, 35 Pages.

Siejko, Krzysztof Z., et al., "Physiological Event Detection Systems and Methods", U.S. Appl. No. 11/276,735, filed Mar. 13, 2006, 56 Pages.

Stein, Emanuel, et al., "Rapid Interpretation of Heart Sounds and Murmurs", Baltimore : Williams & Wilkins, 4th ed., (1997), 85-105.

Tavel, Morton E., "The Appearance of Gallop Rhythm after Exercise Stress Testing", *Clin. Cardiol.*, vol. 19, (1996), 887-891.

Wariar, Ramesh, et al., "Detection of Myocardial Ischemia From the Time Sequence of Implanted Sensor Measurements", U.S. Appl. No. 11/426,835, filed Jun. 27, 2006, 41 Pages.

Weissler, A. M., "Systolic time intervals in heart failure in man", *Circulation*, 37(2), (Feb. 1968),149-59.

Wood, J. C., et al., "Time-Frequency Transforms: A New Approach to First Heart Sound Frequency Dynamics", *IEEE Transactions on Biomedical Engineering*, 39 (7), IEEE Service Center, US,(Jul. 1, 1992), 730-740.

Xu, J., et al., "A new, simple, and accurate method for non-invasive estimation of pulmonary arterial pressure", *Heart 88*, (2002), 76-80.

Zhao, Zhi-Qing, et al., "Inhibition of myocardial injury by ischemic postconditioning during reperfusion: comparison with ischemic preconditioning", *Am J Physiol Heart Circ Physiol*, 285(2), (Aug. 2003), H579-H588.

"U.S. Appl. No. 11/148,107, Notice of Allowance mailed Mar. 30, 2009", 4 pgs.

"U.S. Appl. No. 11/148,107, Response filed Mar. 16, 2009 to Final Office Action mailed Jan. 14, 2009", 9 pages.

* cited by examiner

ISCHEMIA DETECTION USING HEART SOUND TIMING

CROSS-REFERENCE TO RELATED APPLICATIONS

This application is related to the following commonly assigned U.S. patent applications Ser. No. 10/900,570 entitled "DETERMINING A PATIENT'S POSTURE FROM MECHANICAL VIBRATIONS OF THE HEART," filed on Jul. 28, 2004, now issued as U.S. Pat. No. 7,559,901; Ser. No. 10/703,175, entitled "A DUAL USE SENSOR FOR RATE RESPONSIVE PACING AND HEART SOUND MONITORING," filed on Nov. 6, 2003, now issued as U.S. Pat. No. 7,248,923; Ser. No. 10/334,694 entitled "METHOD AND APPARATUS FOR MONITORING OF DIASTOLIC HEMODYNAMICS," filed on Dec. 30, 2002; Ser. No. 10/746,874 entitled "A THIRD HEART SOUND ACTIVITY INDEX FOR HEART FAILURE MONITORING," filed on Dec. 24, 2003, now issued as U.S. Pat. No. 7,115,096; Ser. No. 11/037,275, entitled "METHOD FOR CORRECTION OF POSTURE DEPENDENCE ON HEART SOUNDS," filed on Jan. 18, 2005; Ser. No. 60/631,742 entitled "CARDIAC ACTIVATION SEQUENCE MONITORING FOR ISCHEMIA DETECTION," filed on Nov. 30, 2004; Ser. No. 11/129,050, entitled "METHOD AND APPARATUS FOR CARDIAC PROTECTION PACING," filed on May 16, 2005; and Ser. No. 11/148,107, entitled "ISCHEMIA DETECTION USING HEART SOUND SENSOR," filed on Jun. 8, 2005; each of which is hereby incorporated by reference.

TECHNICAL FIELD

The field generally relates to implantable medical devices and, in particular, but not by way of limitation, to systems and methods for monitoring mechanical activity of the heart.

BACKGROUND

Implantable medical devices (IMDs) are devices designed to be implanted into a patient or subject. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical therapy or to aid a physician or caregiver in patient diagnosis through internal monitoring of a patient's condition. The devices may include electrodes in communication with a sense amplifier to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Heart sounds are associated with mechanical vibrations from activity of a patient's heart and the flow of blood through the heart. Heart sounds recur with each cardiac cycle and are separated and classified according to the activity associated with the vibration. The first heart sound (S1) can be thought of as the vibrational sound made by the heart during tensing of the mitral valve. The second heart sound (S2) can be thought of as marking the beginning of diastole. The third heart sound (S3) and fourth heart sound (S4) can be conceptualized as related to filling pressures of the left ventricle during diastole. Heart sounds are useful indications of proper or improper functioning of a patient's heart. The present inventors have recognized a need for improved sensing of events related to cardiac activity.

SUMMARY

This summary is intended to provide an overview of the subject matter of the present patent application. It is not intended to provide an exclusive or exhaustive explanation of the invention. The detailed description is included to provide further information about the subject matter of the present patent application. This document discusses, among other things, systems and methods for monitoring mechanical functions of the heart. An example includes a heart sound sensor configured to produce a heart sound signal representative of a heart sound, and a signal analyzer circuit in electrical communication with the heart sound sensor. The signal analyzer circuit is configured to establish a baseline time interval between a first detected physiologic cardiovascular event and at least one second detected physiologic cardiovascular event and at least one of the first and second detected physiologic cardiovascular events includes a heart sound event detected using the heart sound signal. The signal analyzer circuit is also configured to determine that an ischemic event occurred when a measured subsequent change from the established baseline time interval occurs with a time constant that is within a specified range of time constants.

A method example includes sensing a heart sound event, the sensing including producing at least one heart sound signal representative of the heart sound event, establishing a baseline time interval between a first detected physiologic cardiovascular event and at least one second detected physiologic cardiovascular event, wherein at least one of the first and second detected physiologic cardiovascular events includes a heart sound event detected from the heart sound signal, and determining that an ischemic event occurred when a measured subsequent change from the established baseline time interval occurs with a time constant that is within a specified range of time constants.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Because heart sounds are a mechanical measure of a patient's hemodynamic system, monitoring of one or more heart sounds can aid a caregiver in detecting overall progression of heart disease. For example, ischemia exhibits an increase in ventricular chamber stiffness and an increase in a degree of restrictive filling, which are correlated to an increase in loudness of S3 heart sounds and/or S4 heart sounds. Conversely, because ischemia is associated with a decrease in ventricular chamber contractility, ischemia is correlated to a decrease in the loudness of the S1 heart sound. When S3 heart sounds are present in patients experiencing acute chest pain, there is an increased likelihood that such pain results from a myocardial infarction relative to other potential causes of chest pain.

An acute myocardial infarction (AMI) will typically completely occlude a coronary artery. It is typically caused by a rupture of plaque in an artery and typically results in a pronounced change in a patient's hemodynamic system. When at least twenty-five percent of the left ventricle becomes acutely ischemic, the end-diastolic pressure and the end-diastolic volume tend to increase, which results in increased loudness of S3 heart sounds, of S4 heart sounds, or of both S3 and S4 heart sounds, depending on the condition of the heart.

Figure 1:
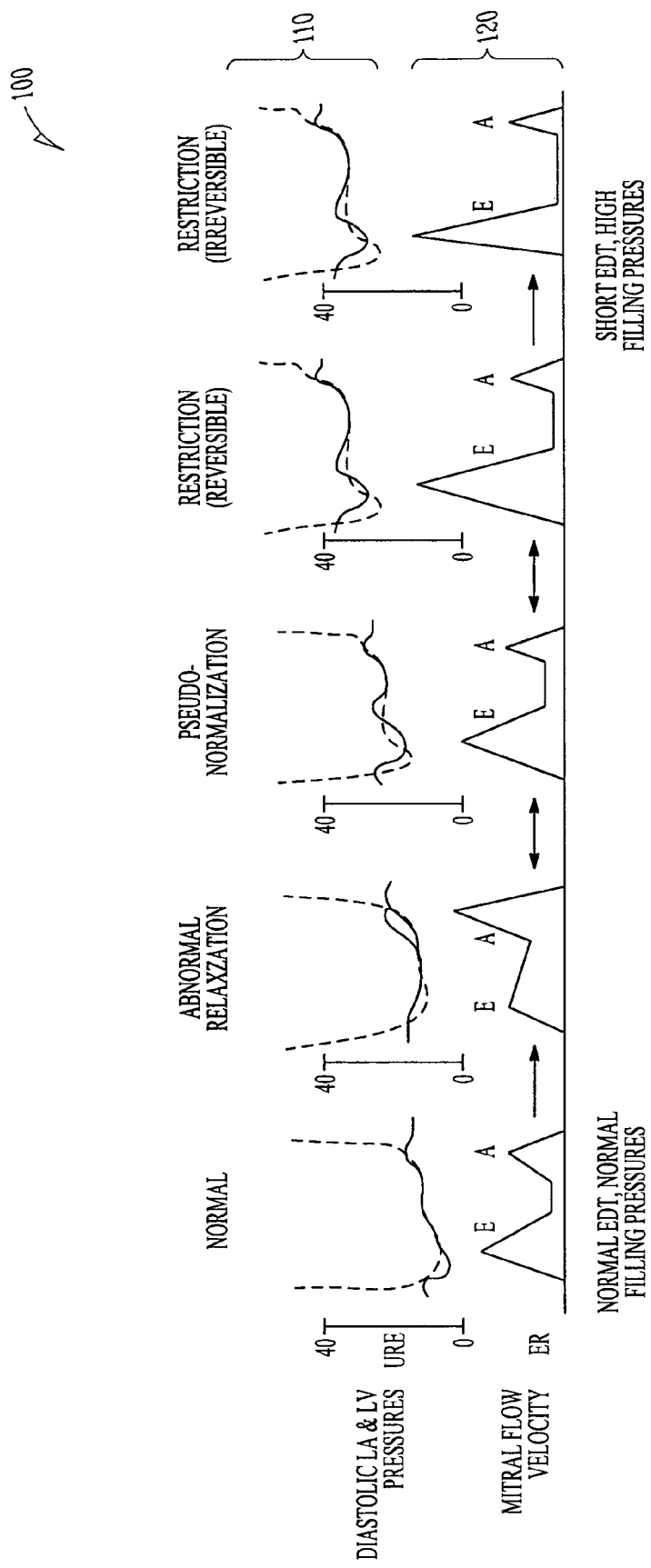
FIG. 1 illustrates an example of progression of heart failure.

FIG. 1 illustrates an example of changes in diastolic pressure with worsening heart failure (HF). FIG. 1 shows graphs 110 of left atrium (LA) and left ventricle (LV) diastolic pressures and graphs 120 of the associated E-wave and A-wave. An E-wave represents the peak mitral flow velocity during passive filling, and an A-wave represents the peak mitral flow velocity during atrial contraction. The graphs 100 represent stages of worsening HF from a normal case on the left to irreversible flow restriction on the right. As the HF condition worsens, the filling time typically shortens and the left ventricular pressure (LVP) and left atrial pressure (LAP) typically become more elevated. Depending on the condition of the heart, this generally results in increased loudness of S3 heart sounds, of S4 heart sounds, or of both S3 and S4 heart sounds. For example, if a baseline of heart sound measurements for a patient is established, a change from the baseline can be a good indication that something has changed in the hemodynamic system of the patient.

The progression of HF is typically accompanied by changes in heart sounds over time. First, an S4 heart sound may develop while the heart is still relatively healthy. Second, the S4 heart sound can become more pronounced. Third, as deterioration of the left ventricle continues, S3 heart sounds typically become more pronounced. Sometimes, this is accompanied by a decrease in S1 heart sounds, due to a decrease in the heart's ability to contract. Thus, ongoing or continuous monitoring of heart sounds would greatly assist caregivers in monitoring heart disease. However, individual patients may exhibit unique heart sounds, which can complicate a generalized approach to heart sound monitoring. For example, the mere presence of an S4 heart sound is not necessarily indicative of heart disease because certain normal patients may have an S4 heart sound. Another complication develops if a patient experiences atrial fibrillation when an ischemia occurs. In this case, a strong atrial contraction, and the associated S4 heart sound, is likely to be absent due to the atrial fibrillation. This can result in an increase in the S3 heart sound without an associated S4 heart sound or without an increase in an S4 heart sound. Therefore, the progression of heart disease, such as HF and an ischemic event, can be better monitored by establishing a patient-specific control baseline heart sound measurement, and then monitoring for changes from that baseline. One or more such baselines could be established in one or several different circumstances, such as at particular physiologic or pathophysiologic state, at a specific posture, at a particular time of day, etc.

Changes due to AMI are typically immediate and typically result in a heart sound change within seconds or minutes. In contrast, heart sound changes due to worsening HF are gradual and occur over hours or days. Therefore, not just the change but the timeframe of the occurrence of the change in heart sounds can be used to detect overall progression of heart disease. Additionally, one or more relationships between heart sounds can be used to determine the likelihood of an ischemic event. For example, the dynamics between the S3 and S4 heart sounds with respect to the HF progression can be used to determine the likelihood that a patient experienced an ischemic event. An appearance of the S3 and S4 heart sounds is more likely to indicate a recent occurrence of an ischemic event if the S4/S3 ratio is high than if the S4/S3 ratio is low, which would instead indicate that a patient is in a more advanced stage of HF.

Implantable medical devices (IMDs) can include one or more sensors, such as to monitor one or more internal patient parameters such as one or more heart sounds. A heart sound sensor can be implemented as an accelerometer monitoring the vibrations associated with heart sounds. Because the devices are implantable, IMDs can be used to provide ongoing or continuous or chronic ambulatory monitoring of one or more of a patient's heart sounds. The implanted device can be used to first establish a baseline for its individual patient during a pre-AMI period. The device can then monitor the one or more patient heart sounds to detect any change from the baseline.

Figure 2:
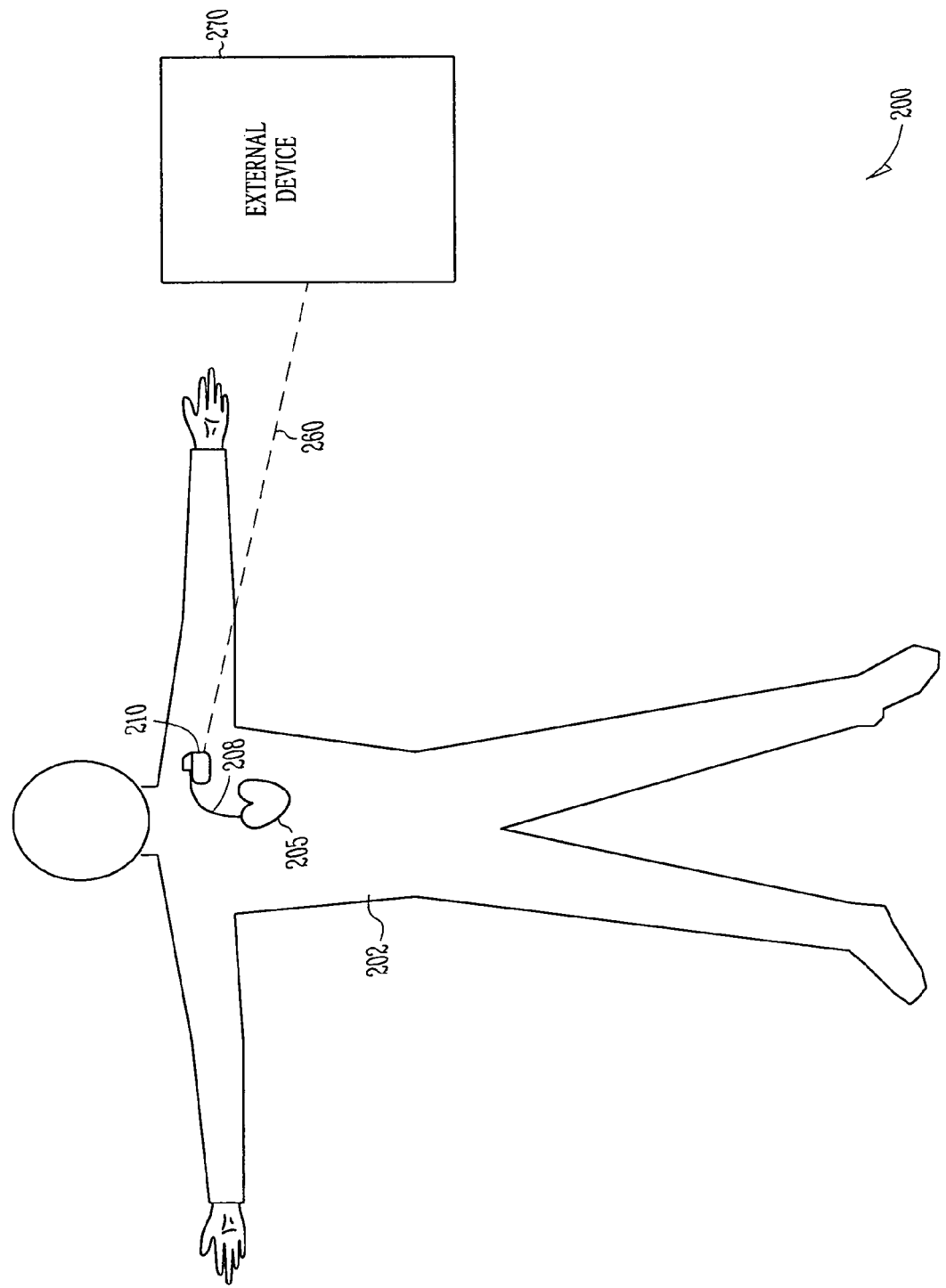
FIG. 2 illustrates an example of portions of a system that uses an implantable medical device.

FIG. 2 illustrates an example of a system 200 that uses an IMD 210. The system 200 shown is one example of portions of a system 200 used to treat a cardiac arrhythmia or otherwise improve heart function. In this example, a pulse generator (PG) or other IMD 210 is coupled to a heart 205 of a patient 202 by a cardiac lead 208, or additional leads. A leadless IMD is also possible, which can provide far-field cardiac signal sensing or therapy delivery. Some examples of IMD 210 include, without limitation, a pacer, a defibrillator, a cardiac resynchronization therapy (CRT) device, or a combination of such devices. Other examples include implantable diagnostic devices, a drug pump, and a neural stimulation device. System 200 also typically includes an IMD programmer or other local or remote external system 270 that provides wireless communication 260 to with the IMD 210, such as by using radio frequency (RF) or other telemetry.

In the example of FIG. 2, a cardiac lead 208 includes a proximal end that is coupled to the IMD 210 and a distal end, coupled by one or more electrodes to one or more portions of a heart 205. The electrodes typically deliver one or more of cardioversion, defibrillation, pacing, or resynchronization therapy, or any permutation or combination thereof to at least one chamber of the heart 205. IMD 210 typically includes electronic or other components that are enclosed in a hermetically-sealed canister or "can." Additional electrodes may be located on the can, or on an insulating header, or on other portions of IMD 210, such as for providing unipolar pacing or defibrillation energy, for example, in conjunction with the electrodes disposed on or around heart 205. The lead 208 or leads and electrodes are also typically used for sensing electrical activity of a heart 205 or other sensing.

Heart sound sensors generally include implantable acoustic sensors that convert the detected sounds of the heart into an electrical signal representative of the heart sounds. For example, an acoustic sensor for an IMD 210 can include an accelerometer mounted within the IMD can. In another sensor example, a microphone is located within the IMD can. In another example, the acoustic sensor can include a strain gauge.

Figure 3:
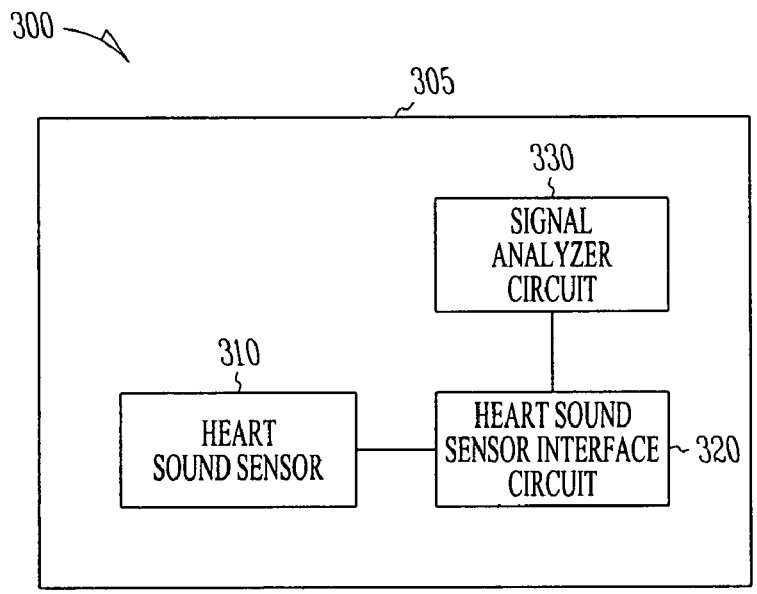
FIG. 3 shows portions of an example of a system for monitoring heart sounds.

FIG. 3 shows portions of an example of a system 300 for monitoring one or more heart sounds. In this example, the system 300 includes a heart sound sensor 310 and a signal analyzer circuit 330 coupled to the heart sound sensor 310. The heart sound sensor 310 produces an electrical signal representative of at least one heart sound. The system 300 may include a heart sound sensor interface circuit 320 between the heart sound sensor 310 and the signal analyzer circuit 330 to provide additional pre-processing to the electrical heart sound signal, such as filtering and/or amplification for example. In some examples, the heart sound sensor and the signal analyzer circuit 330 are included in an external medical device. In some examples, the heart sound sensor and the signal analyzer circuit 330 are included in an implantable medical device (IMD) 305.

The signal analyzer circuit 330 is configured to measure a baseline heart sound signal, such as by being operable to perform an algorithm or algorithms implemented by hardware, software, firmware or any combination of hardware, software or firmware. In some examples, the baseline heart sound signal includes or aggregates a patient's different heart sounds that occur during a cardiac cycle. In certain examples, the baseline signal represents a subset of the different heart sounds that occur during a cardiac cycle, such as one type of heart sound (e.g., one or more of S3, S4, etc.). In one example, the baseline heart sound signal is established for an individual patient during a pre-AMI period. In another example, the baseline is established at time of implant. In yet another example, the baseline is established while a patient is in a known or specified physiologic or pathophysiologic state.

In some examples, the signal analyzer circuit 330 includes an averaging, central tendency, or other compositing circuit. For example, a baseline heart sound signal can be established by forming an ensemble or other average of multiple sampled values of like heart sound signals. One example of techniques for obtaining ensemble averages of heart sounds is found in the commonly assigned, co-pending U.S. patent application Ser. No. 10/746,874 by Siejko et al., entitled "A Third Heart Sound Activity Index for Heart Failure Monitoring," filed on Dec. 24, 2003, which is incorporated herein by reference, including its description of obtaining ensemble averages of heart sounds.

In some examples, the signal analyzer circuit 330 includes a low pass filter circuit. In some examples, the signal analyzer circuit 330 includes a central tendency circuit and establishes a baseline signal by determining the central tendency of multiple sampled values of the heart sound signals. The baseline signal is typically stored in memory in, or coupled to, the signal analyzer circuit 330. In some examples, the baseline signal is loaded into the memory using an external device to communicate with the IMD 305. After the baseline is established, the signal analyzer circuit 330 monitors one or more heart sound signals for any change from the baseline signal. Examples of changes include without limitation, changes in amplitude of one or more heart sounds, changes in intervals between heart sounds, changes in a measured frequency spectrum of one or more heart sounds, and changes in a power spectrum of one or more heart sounds.

In some examples, the baseline signal includes an aggregate of a patient's different heart sound signals and the change includes a change from that aggregate of signals. In some examples, the baseline signal represents a subset of the heart sounds that occur during a cardiac cycle, such as one type of heart sound, and the change includes a change in the one type of heart sound from the baseline of that type of heart sound. In some examples, a sampled segment of the heart sound signal that includes the change is stored in the memory. Some examples of the sampled segment include a segment sampled before the change occurred and a segment sampled after the change occurred. Upon detection of a particular type of change, the signal analyzer circuit 330 declares that a patient has experienced an ischemic event, such as an acute myocardial infarction.

Some examples of changes that may indicate that an ischemic event occurred include, without limitation, an amplitude of at least one heart sound of the heart sound signal, a power spectrum of the heart sound signal, an amplitude of a first heart sound of the heart sound signal normalized with respect to an amplitude of a second heart sound, an amplitude of a first heart sound normalized with respect to a measured power of the heart sound signal measured during systole, a frequency of occurrence of a heart sound in the heart sound signal, a duration of an occurrence of a heart sound in the heart sound signal, and a relative change in a time interval between first and second detected physiological cardiovascular events. The temporal nature of the change may provide further evidence of that an ischemic event occurred. For example, if the measured change from the baseline heart sound signal occurs relatively suddenly with a time constant that ranges from a few seconds to a few minutes, the episode may indicate an ischemic event. If the measured change is gradual and occurs over hours or days, the episode may indicate the change is due to a worsened HF condition.

Once the signal analyzer 330 declares that such an ischemic event has occurred, this information can then be used by the signal analyzer circuit 330 to provide an indication of the occurrence of the ischemic event. In one example, the signal analyzer circuit 330 activates an alarm, such as a buzzer or other user-detectable indication to indicate that an ischemic event occurred. In another example, the IMD 305 includes a communication circuit coupled to the signal analyzer circuit 330 and the IMD 305 communicates information about the measured change from the baseline in the heart sound signal to an external device. In some examples, the external device initiates one or more measurements of one or more heart sounds. In some examples, the IMD 305 transmits the heart sound signal segment stored in memory to the external device. In some examples, the external device includes an IMD programmer and the IMD 305 indicates that an ischemic event has occurred by setting a status indication in the IMD, where such status indication is readable by the external programmer upon a subsequent interrogation of the IMD 305. In another example, the external device includes a communication repeater that serves as an intermediary between the IMD and a remote external device such as a centralized server configured for remote patient monitoring, and the repeater retransmits information from the IMD 305 over a network. In some examples, the external device is in communication with the IMD 305 and a computer network such as a hospital network or the Internet. The indication of the ischemic event or an alarm can then be transmitted to a caregiver using the network. An indication or alarm can also be provided to the patient. This is useful, for example, such as to direct the patient to take a drug, adjust medication, or to seek immediate medical assistance.

Figure 4A:
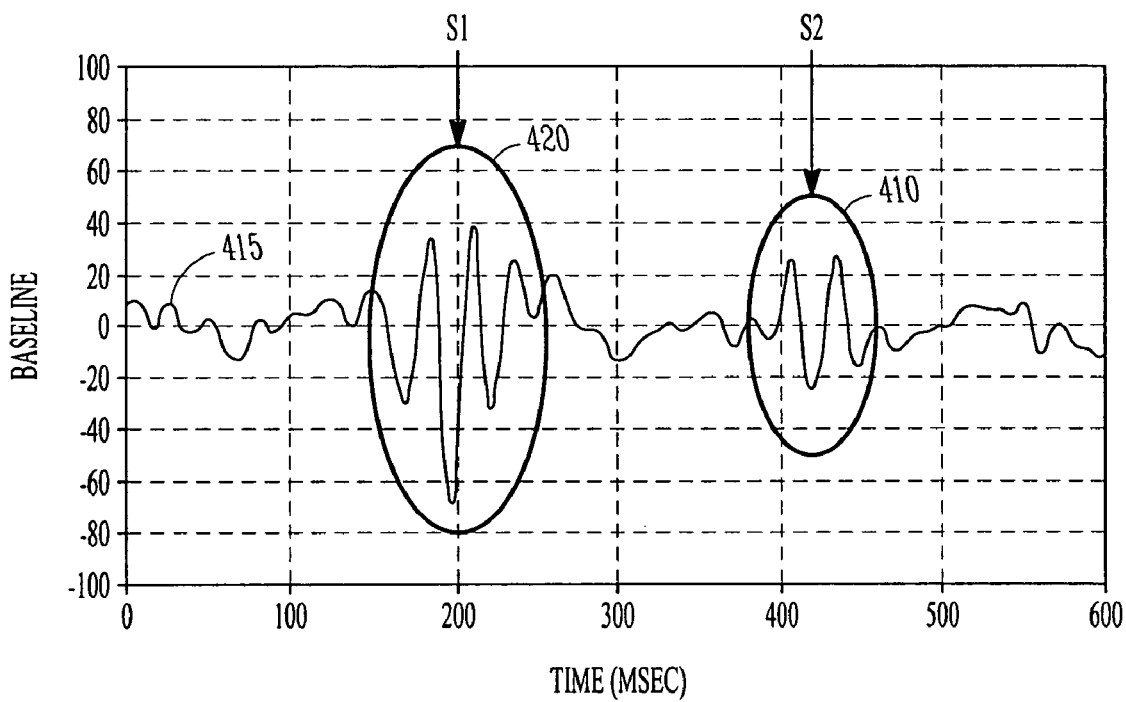
FIGS. 4A-C illustrate an example of heart sound signals obtained from an animal study.
Figure 4B:
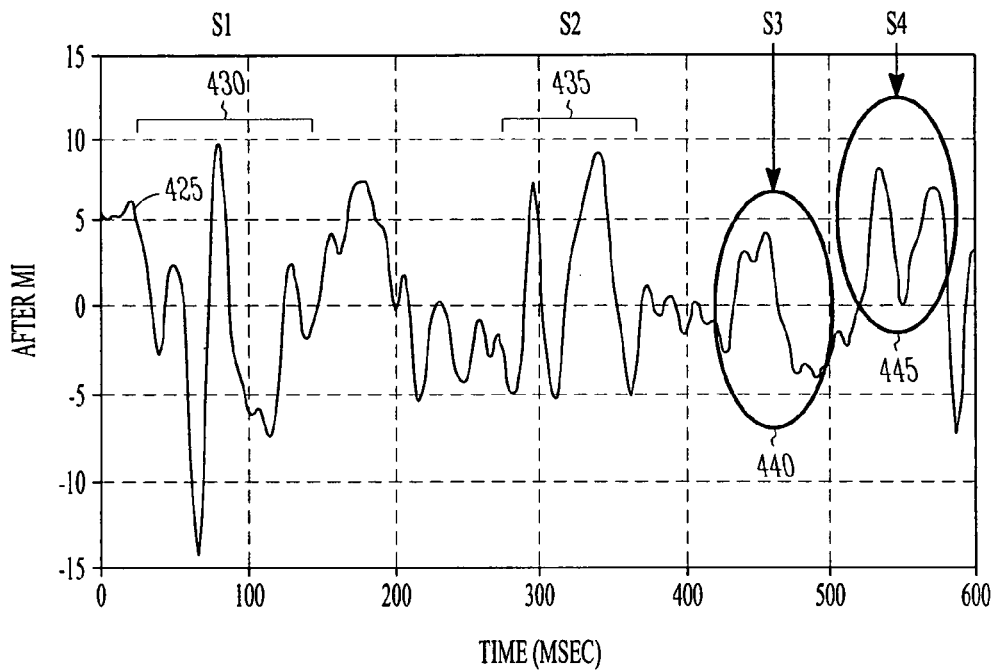
Figure 4C:
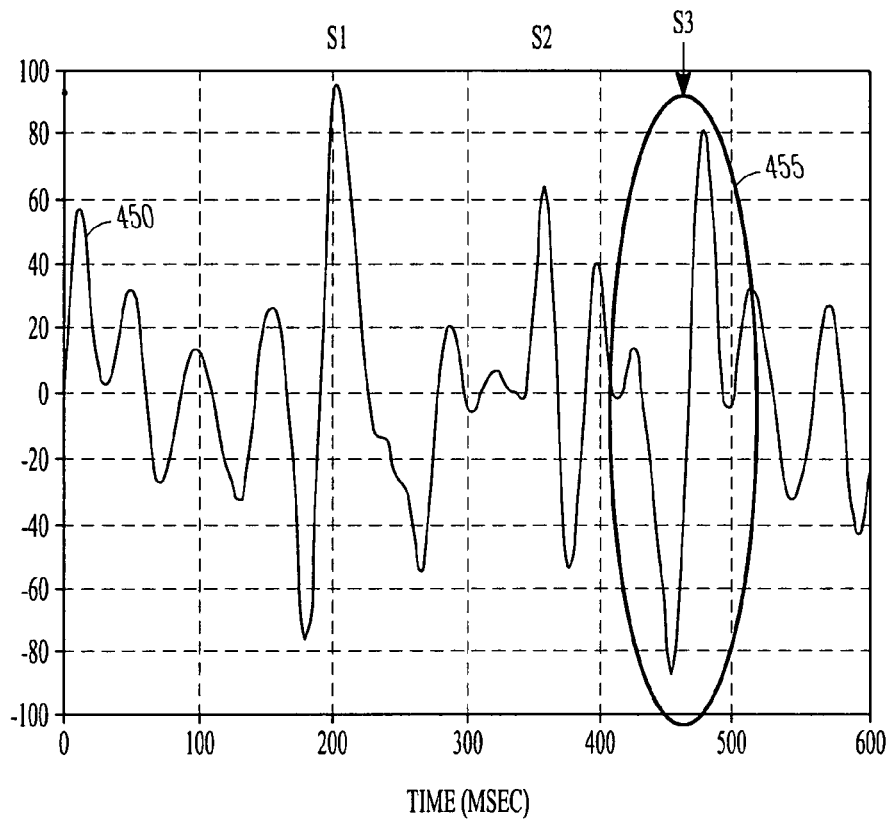

Ischemic events can be detected from a variety of different measured changes from one or more baseline heart sound signals. An example is shown in FIGS. 4A-4C, which illustrate heart sound signals obtained from an animal study. FIG. 4A shows an example of a baseline heart sound signal 410 that was measured using an implanted accelerometer-type heart sound sensor. In this example, the signal 410 includes the S1 heart sound 415 and the S2 heart sound 420. FIG. 4B shows an example of a measured heart sound signal 425 after ischemia was induced in the animal by micro-embolization. In the example of FIG. 4B, the signal 425 includes the S1 heart sound 430, an S2 heart sound 435, and further shows the presence of the S3 heart sound 440 and the S4 heart sound 445. FIG. 4C shows an example of a heart signal 450 after the animal experienced heart failure or heart decompensation. The Example of FIG. 4C shows that the amplitude of the S3 heart sound 455 has increased from that shown in FIG. 4B, and the amplitude of the S3 heart sound has changed (increased) relative to the S1 and S2 heart sounds. FIGS. 4A-C show that in some examples, an ischemic event results in the presence of at least one heart sound (such as the S3 or S4 heart sounds) in the measured signal 425, 450, which is absent from the baseline heart sound signal 410. In some examples, an ischemic event can result in a reduction in amplitude of at least one heart sound, such as the S1 or S2 heart sound, in the measured signal 425, 450 compared to the baseline heart sound signal 410. In some examples, the signal analyzer circuit 330 declares that an ischemic event has occurred using the duration of an occurrence of a heart sound, such as the S3 or S4 heart sound, which is absent from the baseline heart sound signal 410. In some examples, the signal analyzer circuit 330 declares that an ischemic event has occurred from the how often there is an occurrence or re-occurrence of at least one heart sound (such as the S3 or S4 heart sound), which is absent from the baseline heart sound signal 410.

In some examples, the signal analyzer circuit 330 declares that an ischemic event has occurred by measuring a change in amplitude of the measured heart sound from the amplitude of a baseline heart sound. For example, the signal analyzer circuit 330 can measure the amplitude of a particular type of heart sound, such as the S1, S2, S3, or the S4 heart sound, and can compare the measured amplitude to its corresponding baseline amplitude. However, not all patients will exhibit an S3 or S4 heart sound substantially all the time or even most of the time. In some examples, the measured amplitude change is deemed to result from an ischemic event if the measured amplitude change is a specified increase in amplitude of an S3 or S4 heart sound from the corresponding baseline amplitude. In some examples, if the change in amplitude is at least a specified percentage increase from the corresponding baseline amplitude, an ischemic event is deemed to have occurred. In some examples, the measured change is deemed to result from an ischemic event if the measured change is at least a specified decrease in amplitude of an S1 or S2 heart sound from the corresponding baseline amplitude.

In some examples, the signal analyzer circuit 330 establishes a baseline amplitude of a heart sound normalized or otherwise taken relative with respect to another heart sound. Such normalization can include calculating a ratio between at least two different heart sounds associated with the same cardiac cycle. In such an example, the signal analyzer circuit 330 can be configured to declare that an ischemic event occurred when it measures a change in the ratio from a ratio of the corresponding baseline amplitudes, such as, for example, a percentage increase in the ratio from the corresponding baseline ratio. In an example, the amplitude of the S3 or S4 heart sound is normalized with respect to the amplitude of the S1 or S2 heart sound. Because some ischemic events are associated with both an increase in the amplitude of the S3 or S4 heart sound and a decrease of the S1 or S2 heart sound, an advantage of using normalization is that it is more sensitive to some types of ischemic changes than an amplitude measurement alone. In another example, the amplitude of the S4 heart sound is normalized with respect to the S1 heart sound. In another example, the amplitude of the S4 heart sound is normalized with respect to the S3 heart sound to provide an indication of the relative changes between the S3 and S4 heart sound. If the normalization includes a ratio of the heart sounds (S4/S3), in the early stages of heart failure the ratio typically increases with the increase in the S4 heart sound. In later stages, the ratio typically decreases due to the subsequent increase in the S3 heart sound. In some examples, the amplitude of the S1, S3, or S4 heart sound is normalized with respect to the amplitude of the S2 heart sound.

In some examples, the signal analyzer circuit 330 includes a frequency analyzer circuit. This permits the signal analyzer circuit 330 to establish a baseline power spectrum of a heart sound, such as the S1, S2, S3, or S4 heart sound, such as by calculating the power in the heart sound signal in several frequency bands. The signal analyzer circuit 330 declares that an ischemic event has occurred by measuring a change in the power spectrum of a heart sound signal from the corresponding baseline power spectrum. In some examples, the signal analyzer circuit 330 declares that an ischemic event occurred using a heart sound amplitude measurement that is normalized with respect to the calculated power in the signal. In the normalization, a power of the heart sound signal is calculated in several frequency bands. In some examples, the frequency bands include 25 Hz through 60 Hz. In some examples, the frequency bands include 10 Hz through 100 Hz. The calculated power of a specific band of frequencies of the signal is used to normalize the amplitude. As an example, the power calculated from a high frequency band of a heart sound signal sensed during systole can be used to normalize the amplitude of the heart sound.

In some examples, the IMD 305 includes a posture sensor in electrical communication with the signal analyzer circuit 330. The posture sensor produces a posture signal indicative of posture or a change in posture of the subject. The IMD 305 measures heart sound signals in association with a posture or position of a patient. In certain examples, heart sound signals are only measured or used while the patient is in a particular posture (e.g., upright), or measurements made while the patient is in one posture (e.g., upright) are distinguished from measurements made while the patient is in another posture (e.g., lying down). This removes a source of variability of the heart sound signals due to patient posture or position. A description of systems and methods for monitoring heart sounds in association with patient posture are found in commonly assigned, co-pending U.S. patent application Ser. No. 11/037,275 by Siejko et al., entitled "Method for Correction of Posture Dependence on Heart Sounds," filed on Jan. 18, 2005, which is incorporated herein by reference, including its description of using posture information with heart sounds.

In some examples, the IMD 305 measures heart sounds in association with patient activity or other indication of metabolic need. To detect patient activity, some examples of the IMD 305 include a patient activity sensor in electrical communication with the signal analyzer circuit 330. The patient activity sensor produces a signal representative of activity of the patient or subject. If the heart sound sensor and the activity sensor are both accelerometers, a shared or separate accelerometer can be used. In some examples, the IMD 305 infers the patient's activity level from a patient's heart rate, respiration rate, or minute ventilation such as by using a thoracic impedance sensor. In some examples, the IMD 305 declares that an ischemic event has occurred using a measured change in the heart sound signal from at least one corresponding baseline heart sound signal specifically established for exercise conditions. An early or mid-diastolic merging of S3 and S4 heart sounds (i.e., a gallop rhythm) developing after exercise is believed to nearly always signify myocardial disease with reduced myocardial function, including ischemia of heart muscle. Thus, in some examples, an ischemic event can be detected by the presence of the gallop rhythm that is absent from the baseline heart sound signal.

In some examples, a respiration sensor is in electrical communication with the signal analyzer circuit 330. The respiration sensor produces a respiration signal, such as an electrical or optical respiration signal, that includes information about the respiration of the subject. In certain examples, the respiration sensor can include an implantable sensor including at least one of an accelerometer, an impedance sensor, and a pressure sensor. The respiration signal can include any signal indicative of the respiration of the subject, such as inspiration, expiration, or any combination, permutation, or component of the respiration of the subject. In some examples, the signal analyzer circuit 330 measures a heart sound in association with a phase of respiration of the subject. Systems and methods for measuring heart sounds in association with respiration are described in Haro et al., co-pending U.S. patent application Ser. No. 11/561,428, entitled "Respiration-Synchronized Heart Sound Trending," filed Nov. 20, 2006, which is incorporated herein by reference.

In some examples, the signal analyzer circuit 330 uses the temporal nature of changes in one or more heart sounds to distinguish between an ischemic event and an indication of a worsening condition of HF decompensation. For example, if the measured change from the baseline heart sound signal occurs relatively suddenly (e.g., with a time constant that ranges from a few seconds to a few minutes, such as five minutes), the episode can be declared an ischemic event. If the measured change from the baseline heart sound signal occurs with a time constant of several hours (e.g., four hours) or days, the episode can be declared an indication of a worsening condition of HF decompensation. In some examples, the signal analyzer circuit 330 activates the same alarm to indicate HF decompensation as to indicate an occurrence of an ischemic event. In some examples, different alarms indicate HF decompensation or an ischemic event. In some examples, the signal analyzer circuit 330 stores data associated with measured changes from the baseline signal in memory. The signal analyzer circuit 330 can be configured to be capable of calculating trend data of the measured changes and to store the trend data in memory. In some examples, the signal analyzer circuit 330 uses the trend data to generate a heart failure status indication. In some examples, the IMD 305 transmits the trend data to a local or remote external device, such as for analysis or display.

Figure 5:
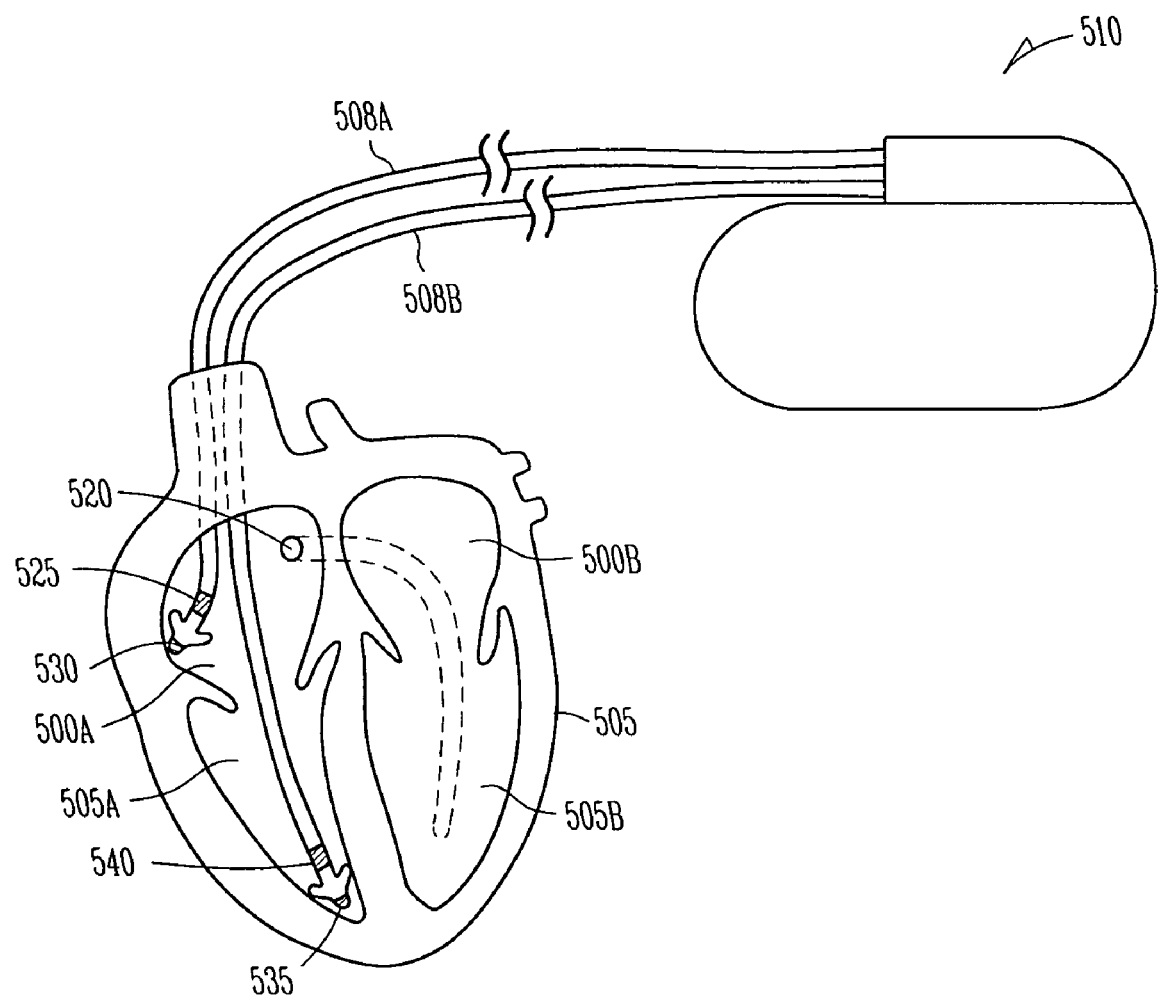
FIG. 5 illustrates an example of an implantable medical device coupled by leads to a heart.

FIG. 5 illustrates an example of an IMD 510 coupled to heart 505, such as by one or more leads 508A-B. Heart 505 includes a right atrium 500A, a left atrium 500B, a right ventricle 505A, a left ventricle 505B, and a coronary vein 520 extending from right atrium 500A. In this embodiment, atrial lead 508A includes electrodes (electrical contacts, such as ring electrode 525 and tip electrode 530) disposed in, around, or near an atrium 500A of heart 505 for sensing signals, or delivering pacing therapy, or both, to the atrium 500A. Lead 508A optionally also includes additional electrodes, such as for delivering atrial cardioversion, atrial defibrillation, ventricular cardioversion, ventricular defibrillation, or combinations thereof to heart 505. Lead 508A optionally further includes additional electrodes for delivering pacing or resynchronization therapy to the heart 505.

Ventricular lead 508B includes one or more electrodes, such as tip electrode 535 and ring electrode 540, for sensing signals, for delivering pacing therapy, or for both sensing signals and delivering pacing therapy. Lead 508B optionally also includes additional electrodes, such as for delivering atrial cardioversion, atrial defibrillation, ventricular cardioversion, ventricular defibrillation, or combinations thereof to heart 505. Such electrodes typically have larger surface areas than pacing electrodes in order to handle the larger energies involved in defibrillation. Lead 508B optionally further includes additional electrodes for delivering pacing or resynchronization therapy to the heart 505.

Other forms of electrodes include meshes and patches which may be applied to portions of heart 505 or which may be implanted in other areas of the body to help "steer" electrical currents produced by IMD 510. In one embodiment, one of atrial lead 508A or ventricular lead 508B is omitted, i.e., a "single chamber" device is provided, rather than the dual chamber device illustrated in FIG. 5. In another embodiment, additional leads are provided for coupling the IMD 510 to other heart chambers and/or other locations in the same heart chamber as one or more of leads 508A-B. The present methods and systems will work in a variety of configurations and with a variety of electrical contacts or "electrodes," including a leadless system that uses electrodes remote from, rather than touching, the heart 505.

Figure 6:
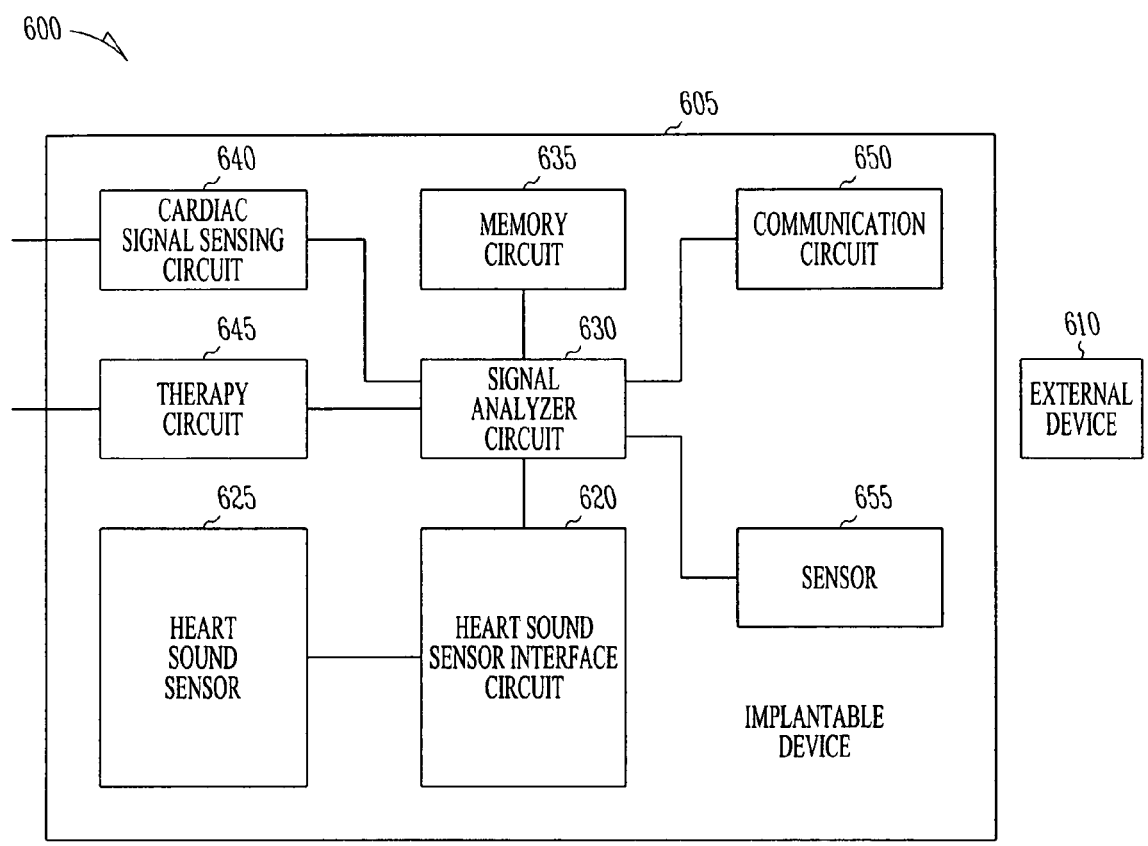
FIG. 6 shows portions of an example of a system for monitoring heart sounds and electrocardiograms.

FIG. 6 shows portions of an example of a system 600 for monitoring heart sounds and electrical cardiac signals. The system 600 includes a heart sound sensor 625 and a signal analyzer circuit 630. The heart sound sensor 625 produces electrical signals representative of at least one heart sound. In some examples, the system includes a heart sound sensor interface circuit 620 coupled to a signal analyzer circuit 630 and the heart sound sensor 625 to provide signal preprocessing, such as signal filtering and amplification for example. In some examples, the system may include a cardiac signal sensing circuit 640. The cardiac signal sensing circuit produces an electrical cardiac signal representative of physiologic cardiac activity of a heart of a subject. In some examples, the heart sound sensor 625 and a signal analyzer circuit 630 are included in an external medical device and the cardiac signal sensing circuit 640 is included in the same or a separate external medical device.

In certain examples, the heart sound sensor 625 and the signal analyzer circuit 630 are included in an IMD 605. The IMD 605 may also include a memory circuit 635 and a therapy circuit 645. In some examples, the system 600 includes the IMD 605 and an external device 610 operable to communicate with the IMD 605. The therapy circuit 645 is coupled to one or more electrodes. In one example, the therapy circuit 645 is attached to a cardiac lead or leads such as to provide cardioversion, defibrillation, pacing, resynchronization therapy, or one or more combinations thereof to at least one chamber of the heart. The memory circuit 635 stores heart sound measurements. In some examples, the memory circuit 635 also stores segments of measured cardiac signals. The IMD 605 further includes a communication circuit 650. The external device 610 communicates wirelessly with the IMD 605 by using RF or other telemetry signals. The IMD 605 communicates heart sound information to the external device 610. In some examples, the external device 610 is part of, or is in communication with, a computer network such as a hospital computer network or the Internet.

The cardiac signal sensing circuit 640 senses electrical cardiac signals associated with the action potential signals of a heart. The action potentials propagate through the heart's electrical conduction system to excite various regions of myocardial tissue. The cardiac signal sensing circuit 640 provides an electrical signal representative of such signals. Examples of cardiac signal sensing circuits 640 include, without limitation, a subcutaneous electrocardiogram (ECG) sensing circuit, an intracardiac electrogram (EGM) sensing circuit, and a wireless ECG sensing circuit. In a subcutaneous ECG sensing circuit, electrodes are implanted beneath the skin and the ECG signal obtained is referred to as subcutaneous ECG or far-field electrogram. In an intracardiac EGM circuit, at least one electrode is placed in or around the heart. A wireless ECG includes a plurality of electrodes to provide differential sensing of cardiac signals to approximate a surface ECG. Descriptions of wireless ECG systems are found in commonly assigned, co-pending U.S. patent application Ser. No. 10/795,126 by McCabe et al., entitled "Wireless ECG in Implantable Devices," filed on Mar. 5, 2004, which is incorporated herein by reference, including its description of a wireless ECG.

The signal analyzer circuit 630 measures the heart sound signal and the cardiac signal. In some examples, the signal analyzer circuit 630 measures the heart sounds in correspondence with a sensed heart depolarization, such as to help identify particular heart sounds. The desired heart sound can be identified by aligning the heart sound signal to known features in a sensed cardiac signal. For example, an R-wave sensed by the cardiac signal sensing circuit 640 helps align S1 and S2 heart sounds sensed with the heart sound sensor 625. This can be useful for, among other things, identifying a time window associated with a particular heart sound, such as when establishing a baseline heart sound signal.

In some examples, the IMD 605 declares that an ischemic event occurred using either the cardiac signal or the heart sound signal. In some examples, the IMD 605 declares that an ischemic event occurred using both a measured change in the cardiac signal from an established baseline cardiac signal and a measured change in the heart sound signal from an established corresponding baseline heart sound signal. Using both signals to conclude that an ischemic event occurred increases the confidence or specificity in the conclusion. As an example, the signal analyzer circuit 630 declares that an ischemic event has occurred using a specified measured minimum change from the corresponding baseline heart sound signal and a sensed cardiac signal having an S-wave to T-wave ("ST") interval that deviates by at least a specified amount from an ST interval of a baseline cardiac signal. In another example, the signal analyzer circuit 630 declares an ischemic event to have occurred upon detecting at least a specified measured change in the heart sound signal and a sensed cardiac signal having a T-wave that is inverted from the T-wave in the baseline cardiac signal. In another example, the signal analyzer circuit 630 declares an ischemic event to have occurred upon detecting at least a specified measured change in the heart sound signal and a sensed cardiac signal having a sensed T-wave that is biphasic relative to a monophasic T-wave in the baseline cardiac signal. Descriptions of systems and methods for detecting ischemia using wireless ECG circuits are found in commonly assigned, co-pending U.S. patent application Ser. No. 60/631,742 by Zhang et al., entitled "Cardiac Activation Sequence Monitoring for Ischemia Detection," filed on Nov. 30, 2004, which is incorporated herein by reference, including its description of systems and method for detecting ischemia using wireless ECG circuits.

In some examples, a surface ECG sensing circuit is coupled to the external device. The ECG sensing circuit includes at least two electrodes attached to the skin of a patient to sense cardiac signals. The external device then declares that an ischemic event occurred using both a measured change in an ECG signal obtained from the external ECG circuit and a measured change in the heart sound signal obtained from the IMD 605.

In some examples, the signal analyzer circuit 630 declares that an ischemic event has occurred using a temporal relationship between the measured change in the heart sound signal and the sensed event indicated by the cardiac signal. In one such example, the signal analyzer circuit 630 declares an ischemic event to have occurred by detecting a sequence in time of heart sound signal changes and cardiac signal changes. As an illustrative example of such a sequence of events, the signal analyzer circuit 630 may first measure a decrease in the S1 heart sound signal from the S1 baseline. The signal analyzer circuit 630 subsequently measures a deviation in the ST interval of the cardiac signal from the baseline cardiac signal. Later, an S3 heart sound appears on the measured heart sound signal, where the S3 heart sound is absent in the baseline heart sound signal. When such a sequence occurs, the signal analyzer circuit 630 declares that an ischemic event has occurred. As another example, the cardiac signal T-waves discussed above typically disappear after about one hour following an ischemic event, but the evidence from heart sound changes remains. In one example, the signal analyzer circuit 630 declares that an ischemic event has occurred when the cardiac signal feature appears temporarily (e.g., for a time period of less than about one hour), but the heart sound signal changes from baseline persist, even after the temporary cardiac signal feature subsides.

In some examples, the signal analyzer circuit 630 uses one or more rules to combine the outputs of the cardiac signal sensing circuit 640 and the heart sound sensor interface circuit 620. In one example, the signal analyzer circuit 630 assigns at least a first weight to the measured change from baseline in the heart sound signal and assigns at least a second weight to a sensed event indicated by the change in the ECG signal. The signal analyzer circuit 630 then declares an ischemic event to have occurred according to at least one rule incorporating the measured change in the heart sound signal, the sensed event indicated by the ECG signal and the assigned weights. Table 1 below shows an example in which the applied rule includes a decision matrix. The signal analyzer circuit 630 applies a low, medium, or high weight to the strength of a measured S4 heart sound change. Similarly, the signal analyzer circuit 630 applies a low, medium, or high weight to a measured deviation in an ST interval in an ECG signal. In one example, the weights are applied based on amplitude changes from a corresponding patient-specific baseline.

TABLE 1

ST deviation

| | Low | Medium | High |
|---|---|---|---|
| High | – | – | High Confidence Level |
| Medium | – | – | – |
| Low | Low Confidence Level | – | – |

S4 Heart Sound

If the weights of the measured signals are both low, the signal analyzer circuit 630 has a low confidence level that an ischemic event occurred. If the weights of the measured signals are both high, the signal analyzer circuit 630 has a high confidence level that an ischemic event occurred. The rest of the decision matrix can be programmed, such as based on factors such as history of the patient or experience of the caregiver.

In some examples, the IMD 605 includes one or more other physiologic or other sensors 655, such as to measure patient posture, patient activity, intracardiac or trans-thoracic impedance, or blood pressure. In some examples, the signal analyzer circuit 630 uses at least one rule to blend the outputs of the various sensors to make a decision as to whether a patient has experienced an ischemic event. In some examples, the signal analyzer circuit 630 assigns weights to corresponding outputs of the sensors, and applies at least one rule to combine the sensor outputs and the measured change in the heart sound signal using the weights. The signal analyzer circuit 630 can then determine whether an ischemic event occurred based on the application of the rule. In some examples, the signal analyzer circuit 630 applies one or more fuzzy logic rules that use the weights to merge the sensor outputs and the measured change in the heart sound signal to determine whether an ischemic event occurred.

In some examples, the signal analyzer circuit 630 discriminates a transient ischemic event from an AMI event using a measured change in a heart sound signal from an established baseline heart sound signal. Sometimes an ischemic event detectable by the system 600 may be a transient ischemic event. Transient ischemic events can occur in non-emergency situations, such as a result of exercise, for example. In an example, the signal analyzer circuit 630 discriminates a transient ischemic event from an AMI event based on the duration of the measured subsequent change from the established heart sound signal. As an illustrative example, the signal analyzer circuit 630 declares an ischemic event a transient event when a heart sound (such as an S3 or S4 heart sound, or a combination of S3 and S4 heart sounds) not present in the established baseline signal briefly appears and then disappears from the heart sound signal. In another example, the signal analyzer circuit 630 discriminates a transient ischemic event from an AMI event based on a change in amplitude of a heart sound. As an illustrative example, the signal analyzer circuit 630 may deem that a change in amplitude is a transient ischemic event if the amplitude change is below a predetermined threshold change value and an AMI event if the change is above the change value.

In yet another example, the signal analyzer circuit 630 discriminates a transient ischemic event from an AMI event based on a temporal relationship of a sensed event indicated by a sensed cardiac signal and the measured subsequent change in the heart sound signal from the established baseline heart sound signal. In certain examples, if the signal analyzer circuit 630 detects a change in both the cardiac signal and the heart sound signal, but the cardiac signal change goes away while the heart sound change remains, the signal analyzer circuit 630 declares the event an AMI event. If the signal analyzer circuit 630 detects a change in the cardiac signal but the heart sound signal does not change, the signal analyzer circuit 630 declares the event a transient ischemic event. In some examples, an indication of AMI events or both indications of AMI events and transient ischemic events are stored in the memory circuit 635, communicated to the external device 610, or both stored in the memory circuit 635 and communicated to the external device 610.

According to some examples, the signal analyzer circuit 630 determines that an ischemic event occurred from a relative change in an interval of time between a first detected physiologic cardiovascular event and at least one second detected physiologic cardiovascular event. One of the physiologic cardiovascular events may include a detected heart sound event.

As the result of an ischemic event, contractility of the heart may change. When approximately twenty-five percent of the myocardium of the left ventricle becomes ischemic, the left ventricular end diastolic pressure (LVEDP) may rise. This may happen because the atrial pressure itself may rise, or because a larger atrial kick develops to compensate for the changed contractility of the ventricle. The pre-ejection period (PEP) may also rise. The rise in pressure may lead to a smaller change in pressure (dP/dt) during filling and ejection of the left ventricle.

Figure 7:
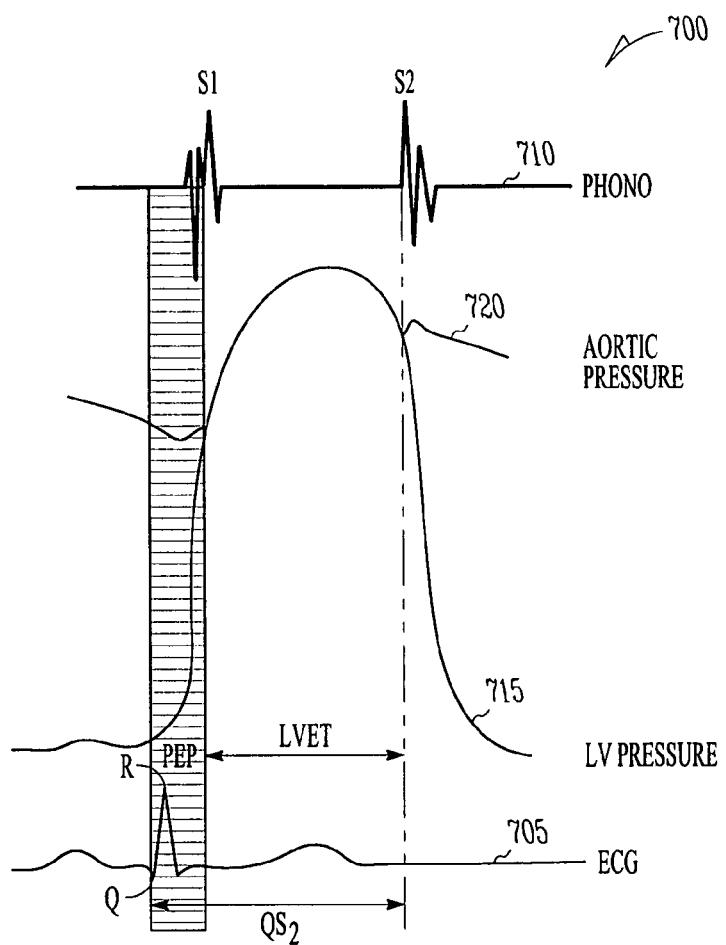
FIG. 7 is an illustration of an example of portions of a cardiac cycle.

FIG. 7 is a conceptualized illustration (not real data) of an example of portions of a cardiac cycle 700. The illustration includes an ECG signal 705 that includes a QRS complex, a heart sound signal 710 that includes the S1 and S2 heart sounds, and waveforms 715, 720 representing aortic and left ventricular pressure. Surrogate measurements for intervals such as PEP can be used to monitor cardiac output.

PEP can be viewed as the time between an R-wave to the opening of the aortic valve. The end of S1 heart sound may include an aortic component associated with an opening of the aortic valve. Thus, an indication of an increase in PEP can be detected from a measured increase in a time interval from the R-wave to the S1 heart sound (R-S1). However, as a result of an ischemic event, the Q-R interval of the QRS complex may also increase. This information related to the changed Q-R interval may be lost if only the interval R-S1 is measured. Thus, an indication of an increase in PEP can be detected from a measured increase in a time interval from the Q-wave to the S1 heart sound (Q-S1), and would be a more sensitive measurement of an indication of PEP than the R-S1 interval. An indication of an increase in PEP can also be detected from a measured increase in a time interval from the Q-wave to the S2 heart sound (Q-S2).

Because of the increase in chamber pressure and lengthening of the Q-S1 time interval, the left ventricular ejection time (LVET) typically decreases in response to an ischemic event. FIG. 7 shows that a surrogate measurement of LVET may include the time between a sensed S1 heart sound and a sensed S2 heart sound (S1-S2). Thus, an ischemic event may be determined from a decrease in a measured S1-S2 interval. Even though S1 to S2 may decrease due to an ischemic event, it should be noted that such an S1 to S2 decrease is not inconsistent with an increase in Q-S2 during an ischemic event. Generally, the decrease in S1-S2 is not large enough to cause a net decrease in the time interval Q-S2 in response to ischemia.

An increase in ventricular pressure may result in a decrease in the time from an opening of the aortic valve to a closing of the aortic valve. The end of S1 heart sound includes an aortic component that may be associated with an opening of the aortic valve. This occurs later in the S1 heart sound, such as during a second half of the S1 heart sound or near a substantial end of an S1 heart sound. The S2 heart sound includes an aortic component that may be associated with a closing of the aortic valve. This occurs early on the S2 heart sound, such during the onset of the S2 heart sound. Therefore, an indication of increased atrial pressure and a possible ischemic event can be determined from a decrease in a measured interval from an aortic component of the S1 heart sound to the aortic component of the S2 heart sound.

As shown in FIG. 4A, a substantial end of an S1 heart sound may be measured by using amplitude of the heart sound. The end of the heart sound can be detected when a local peak of the heart sound dissipates to a specified fraction or percentage of the maximum peak or global peak. Thus, an example of measuring the measured interval from an aortic component of the S1 heart sound to the aortic component of the S2 heart sound is to measure the interval from the substantial end of the S1 heart sound to the onset of the S2 heart sound.

The beginning of the S1 heart sound may include a mitral component associated with closing of the mitral valve. An ischemic event may be reflected in a change in a time duration or width of the S1 heart sound. This may be due to an early closing of the mitral valve following an atrial contraction. Therefore, an occurrence of an ischemic event may be determined from an increase in a time duration (or width) of the S1 heart sound measured from a beginning (or a detected onset) of an S1 heart sound to an end (or a detected substantial end) of the S1 heart sound.

Higher ventricular pressure causes filling of the left ventricle to happen sooner. Therefore, an occurrence of an ischemic event may be determined from a shortening of a measured interval from the S2 heart sound to the S3 heart sound (S2-S3). Because the pressure of the left atrium may rise, the S4 heart sound may occur earlier. Therefore, an occurrence of an ischemic event may be determined from a decrease in a measured interval from the S3 heart sound to the S4 heart sound (S3-S4), or from the S2 heart sound to the S4 heart sound (S2-S4). Similar to the Q-S1 interval, because S1 may be delayed by an ischemic event, the occurrence of an ischemic event may be determined from an increase in a measured interval from the S4 heart sound to the S1 heart sound (S4-S1).

Figure 8:
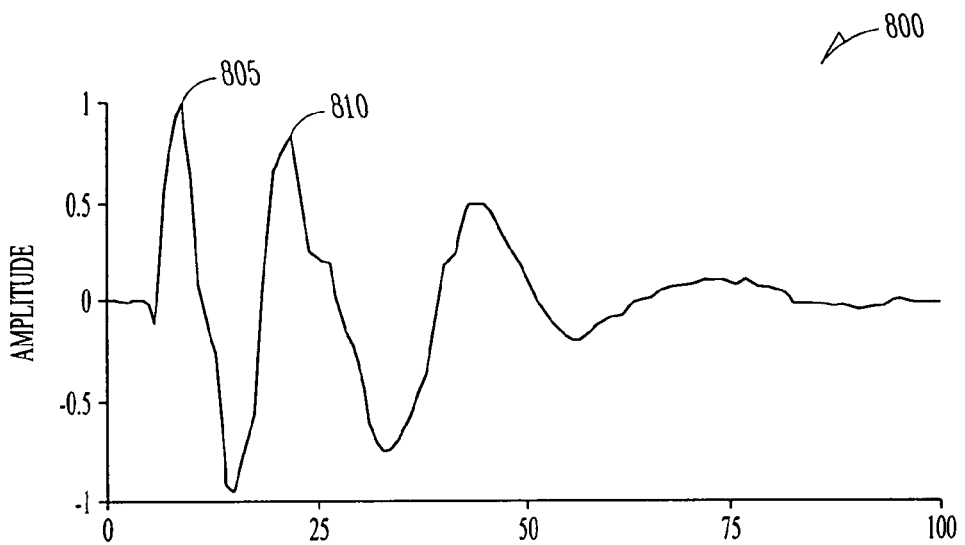
FIG. 8 is an illustration of a graph of an S2 heart sound in the time domain.

FIG. 8 is an illustration of a graph of an S2 heart sound 800 in the time domain. The S2 heart sound includes an aortic component that may be associated with a closing of the aortic valve and a pulmonary component that may be associated with a closing of the pulmonary valve. Typically, the pulmonary valve closure is delayed during an inspiratory phase of respiration of the subject. This may cause two identifiable peaks in the S2 heart sound. The first peak 805 is the aortic component and the second peak 810 is the pulmonary component. The interval of time between these two peaks 805, 810 is sometimes referred to as the S2 split time. An increase in the splitting may be due to an underlying heart condition such as a development of pulmonary hypertension. Thus, the occurrence of an ischemic event may be determined from an increase in the interval between the aortic component and the pulmonary component of the S2 heart sound.

In some examples, to detect an ischemic event, the signal analyzer circuit 630 measures a baseline time interval between a first detected physiologic cardiovascular event and at least one second detected physiologic cardiovascular event. To establish a baseline time interval, the signal analyzer circuit 630 may form an ensemble or other average or central tendency or composite of multiple measured time intervals. The signal analyzer circuit 630 can declare that an ischemic event occurred when a measured subsequent interval change from the established baseline time interval occurs.

The signal analyzer circuit 630 uses the temporal nature of a change in one or more intervals to determine that the change may be due to an ischemic event. To distinguish an ischemic event, a measured change from the established baseline time interval is a change that occurs with a time constant that is within a specified range of time constants. In certain examples, if the measured change from the baseline heart sound signal occurs relatively suddenly, the episode is deemed to be an ischemic event. In certain examples, if the measured change occurs with a time constant that ranges from a few seconds to a few minutes, such as five minutes, the episode is deemed to be an ischemic event.

In some examples, the measured change in an interval must exceed a specified threshold interval change. An ischemic event or a worsening condition of HF may change the nature of a physiologic indication used to detect the ischemic event. In some examples, the signal analyzer circuit 630 re-establishes a baseline heart sound signal if the signal analyzer circuit determines an ischemic event has occurred. In some examples, the signal analyzer circuit 630 re-establishes a baseline heart sound signal if the signal analyzer circuit determines that the subject is experiencing a worsening progression of HF.

In certain examples, at least one of the first and second detected physiologic cardiovascular events includes a specified heart sound. In some examples, the first detected physiologic cardiovascular event includes an R-wave of a QRS complex sensed using a cardiac signal sensing circuit 640, and the second detected physiologic cardiovascular event includes an S1 heart sound detected during the same cardiac cycle using the heart sound sensor 625 (R-S1). The signal analyzer circuit 630 may determine that an ischemic event occurred from an increase in the R-S1 interval from a baseline R-S1 interval, e.g., by a specified threshold value. In some examples, the first detected physiologic cardiovascular event includes a sensed Q-wave of a QRS complex and the second detected physiologic cardiovascular event includes a heart sound detected during the same cardiac cycle, such as an S1 heart sound or an S2 heart sound, for example. The signal analyzer circuit 630 may determine that an ischemic event occurred from an increase in the either the Q-S1 interval or the Q-S2 interval from a baseline time interval, e.g., an increase that meets or exceeds a threshold value.

In some examples, both the first and second detected physiologic cardiovascular events include heart sounds. For example, the signal analyzer circuit 630 may measure the S1-S2 interval for a cardiac cycle and determine that an ischemic event occurred from a specified decrease in the S1-S2 interval from a baseline S1-S2 interval. In some examples, the signal analyzer circuit 630 may measure the S2-S3 interval for a cardiac cycle and determine that an ischemic event occurred from a specified decrease in the S2-S3 interval from a baseline S2-S3 interval. In some examples, the signal analyzer circuit 630 may measure the S4-S1 interval for a cardiac cycle and determine that an ischemic event occurred from a specified increase in the S4-S1 interval from a baseline S4-S1 interval. In some examples, the signal analyzer circuit 630 may measure the S2-S4 interval for a cardiac cycle and determine that an ischemic event occurred from a specified decrease in the S2-S4 interval from a baseline S2-S4 interval. In some examples, the signal analyzer circuit 630 may measure the interval from an aortic component of an S1 heart sound to an aortic component of the S2 heart sound for a cardiac cycle and determine that an ischemic event occurred from a specified decrease in the interval from a baseline time interval. In some examples, the signal analyzer circuit 630 may measure the interval from an onset of a mitral component of an S1 heart sound to an aortic component of an S1 heart sound and determine that an ischemic event occurred from a specified increase in the interval.

In some examples, the signal analyzer circuit 630 may determine that an ischemic event occurred from an increase in a split time of the S2 heart sound. In certain examples, the signal analyzer circuit 630 measures the interval by setting a window around an S2 complex. Setting the window may be done based on a prediction of when S2 occurs in a cardiac cycle for the subject according to multiple cardiac cycles. The signal analyzer circuit 630 detects a peak in the S2 window and labels it an S2 location in the heart signal. The signal analyzer circuit then detects the two largest peak to peak transitions in the S2 window. In certain examples, the signal analyzer includes a peak detector and a bandpass filter circuit with a pass band of 25-60 Hz to detect the peaks. The two largest peak to peak transitions in the S2 window are identified and the interval between the peaks is measured and determined to be the S2 split time.

In some examples, the signal analyzer circuit 630 detects an increase in the S2 split time from a measured increase in the S2 time duration or width. In some examples, the signal analyzer circuit 30 includes a frequency analyzer circuit and detects an increase in the S2 split time using a time-frequency analysis of the S2 heart sound. The signal analyzer circuit 630 computes a time-frequency representation of the S2 window using a Fourier transform when the S2 window is updated. The S2 split time is measured using the interval between the dominant peaks of the resulting time frequency representation. Descriptions of systems and methods to measure the S2 split time are found in Brockway et al., U.S. Patent Application Publication No. 20060020294, entitled "Method and Apparatus for Optimization of Cardiac Resynchronization Therapy Using Heart Sounds," filed Jan. 10, 2004, which is incorporated herein by reference.

The S2 split time may vary for subject according to the posture or the respiration of the subject. In some examples, the signal analyzer circuit 630 is in electrical communication with a posture sensor or a respiration sensor. The signal analyzer circuit 630 measures the S2 split time in association with a specific posture or part of a respiration cycle, or both. In some examples, the signal analyzer circuit 630 may establish a baseline for only one posture or only one part of a respiration cycle of the subject. In some examples, the signal analyzer circuit 630 is in electrical communication with a memory and stores multiple baselines according to multiple postures or multiple parts of a respiration cycle. The signal analyzer circuit 630 may determine that an ischemic event occurred if a measured S2 spilt time exceeds an established baseline S2 split time by a specified threshold.

As described above, surrogate measurements for PEP and LVET intervals can be used to monitor cardiac output. Information derived from these intervals may be useful in monitoring cardiac output. For example, the ratio PEP/LVET is inversely correlated to cardiac output. The ratio PEP/LVET will generally increase with ischemia. Also, an increase in PEP may indicate ischemia while a decrease in LVET may indicate ischemia. Hence, a ratio of a surrogate measurement of PEP to a surrogate measurement of LVET may be more accurate than either of the surrogate measurements alone.

In some examples, the signal analyzer circuit 630 uses at least first and second intervals between detected physiologic events to detect an ischemic event. The first interval is between first and second physiologic events and one of the first and second events may include at least one first heart sound event obtained from a heart sound signal. The second interval can be between third and fourth physiologic cardiovascular events. In some examples, at least one of the third and fourth physiologic cardiovascular events includes a second heart sound event detected during the same cardiac cycle. The second heart sound event can be the same as, or different from, the first heart sound event.

The signal analyzer circuit 630 establishes a baseline measurement for the first time interval and a baseline measurement for the second time interval. The signal analyzer circuit 630 then uses both the first and second baseline time intervals to determine a relative baseline calculation. The signal analyzer circuit 630 may determine that an ischemic event occurred using a measured subsequent change from the established relative baseline calculation, such as where such measured subsequent change exceeds a specified amount.

In some examples, the first interval begins with an R-wave sensed by the cardiac signal sensing circuit 640 and ends with an S1 heart sound sensed by the heart sound sensor 625 during the same cardiac cycle. The second interval begins with the sensed S1 heart sound and ends with an S2 heart sound sensed by the heart sound sensor 625 during the cardiac cycle. The signal analyzer circuit 630 computes a function of the first and second intervals, such as a ratio including the first interval and the second interval [e.g., (R-S1)/(S1-S2), or (S1-S2)/(R-S1)]. The signal analyzer circuit 630 may determine that an ischemic event occurred, such as from a specified increase in the (R-S1)/(S1-S2) ratio from a baseline value of the ratio. (Of course, if the inverse of the ratio is used, the signal analyzer circuit 630 would determine that an ischemic event occurred from a specified decrease in the (S1-S2)/(R-S1) ratio from a baseline value of the ratio.)

In some examples, the first interval begins with an R-wave sensed by the cardiac signal sensing circuit 640 and ends with an S1 heart sound sensed by the heart sound sensor 625 during the same cardiac cycle. The second interval is a time duration between cardiac cycles, such as an R-wave to R-wave interval (R-R). Other indications of a cardiac cycle interval can be used, such as a P-wave to P-wave interval (P-P) for example. The signal analyzer circuit 630 computes a function of the first and second intervals, such as a ratio including the first interval and the second interval [e.g., (R-S1)/(R-R), or (R-R)/(R-S1)]. The signal analyzer circuit 630 may determine that an ischemic event occurred, such as from a specified increase in the (R-S1)/(R-R) ratio from a baseline value of the ratio for example.

In some examples, the first interval begins with a Q-wave sensed by the cardiac signal sensing circuit 640 and ends with an S1 heart sound sensed by the heart sound sensor 625 during the same cardiac cycle. The second interval begins with the sensed S1 heart sound and ends with an S2 heart sound sensed by the heart sound sensor 625 during the cardiac cycle. The signal analyzer circuit 630 computes a function of the first and second intervals, such as a ratio including the first interval and the second interval [e.g., (Q-S1)/(S1-S2), or (S1-S2)/(Q-S1)].

The signal analyzer circuit 630 may determine that an ischemic event occurred, such as from a specified increase in the (Q-S1)/(S1-S2) ratio from a baseline value of the ratio for example.

In some examples, the first interval includes a Q-S1 interval of a cardiac cycle and the second interval begins with the sensed S2 heart sound and ends with an S3 heart sound sensed by the heart sound sensor 625 during the same cardiac cycle. The signal analyzer circuit 630 computes a function of the first and second intervals, such as a ratio including the second interval and the first interval [e.g., (S2-S3)/(Q-S1), or (Q-S1)/S2-S3)]. The signal analyzer circuit 630 may determine that an ischemic event occurred, such as from a specified decrease in the (S2-S3)/(Q-S1) ratio from a baseline value of the ratio for example.

In some examples, the first interval includes a time duration of systole and the second interval includes a time duration of diastole. A systolic time interval can be determined from an interval between S1 and S2 heart sound of the same cardiac cycle "A" ($S1_A$-$S2_A$), and the diastolic time interval can be determined from an interval between the same S2 heart sound of cardiac cycle A and the S1 heart sound of the subsequent cardiac cycle "B" ($S2_A$-$S1_B$). The signal analyzer circuit 630 computes a function of the first and second intervals, such as a ratio including the first interval and the second interval [e.g., ($S1_A$-$S2_A$)/($S2_A$-$S1_B$), or ($S2_A$-$S1_B$)/($S1_A$-$S2_A$)]. The signal analyzer circuit 630 may determine that an ischemic event occurred, such as from a specified increase in the ($S1_A$-$S2_A$)/($S2_A$-$S1_B$) ratio from a baseline value of the ratio for example.

Sometimes it may prove difficult to detect the S1 heart sound. In some examples, the Q-wave (Q) is used as a surrogate for the S1 heart sound. The systolic time interval can be determined from an interval between Q and S2 heart sound of the same cardiac cycle ($Q_A$-$S2_A$), and the diastolic time interval can be determined from an interval between the same S2 heart sound and the Q-wave of the subsequent cardiac cycle ($S2_A$-$Q_B$). The signal analyzer circuit 630 computes a function of the first and second intervals, such as a ratio including the first interval and the second interval [e.g., ($Q_A$-$S2_A$)/($S2_A$-$Q_B$), or ($S2_A$-$Q_B$)/($Q_A$-$S2_A$)]. The signal analyzer circuit 630 may determine that an ischemic event occurred, such as from a specified increase in the ($Q_A$-$S2_A$)/($S2_A$-$Q_B$) ratio from a baseline value of the ratio for example.

In some examples, the first interval begins with the sensed S2 heart sound and ends with an S3 heart sound sensed by the heart sound sensor 625 during the same cardiac cycle. The second interval begins with the sensed S2 heart sound and ends with an S4 heart sound sensed by the heart sound sensor 625 sensed during the cardiac cycle. The signal analyzer circuit 630 computes a function of the first and second intervals, such as a ratio including the first interval and the second interval [e.g., (S2-S3)/(S2-S4), or (S2-S4)/(S2-S3)]. The signal analyzer circuit 630 may determine that an ischemic event occurred, such as from a specified decrease in the (S2-S3)/(S2-S4) ratio from a baseline value of the ratio for example.

In some examples, the system 600 includes another sensor 655 coupled to the signal analyzer circuit 630, such as a posture sensor, for example. In some examples, the second sensor 655 is included in the IMD 605. The IMD 605 measures a baseline time interval in association with a measured posture or position of a patient. In certain examples, the time intervals may only be measured or used while the patient is in a particular posture (e.g., upright). In certain examples, the time intervals measured while the patient is in one posture (e.g., upright) may be distinguished from measurements made while the patient is in another posture (e.g., lying down), such as by storing posture information along with the measured time interval information. By measuring time intervals in association with a measured posture, this removes a source of variability of the time intervals due to patient posture.

In some examples, the sensor 655 includes an activity sensor. The IMD 605 measures a baseline time interval in association with measured patient activity, for example, such as described above with respect to measurement in association with posture or position. In some examples, the signal analyzer circuit 630 determines that an ischemic event has occurred using a measured change in an interval, such as an S3-S4 interval, for example, from at least one corresponding baseline time interval, wherein the baseline time interval is specifically established for a particular state of exercise or activity.

In some examples, the second sensor 655 includes a respiration sensor. The respiration sensor can include an implantable sensor including at least one of an accelerometer, an impedance sensor, and a pressure sensor. The respiration signal can include any signal indicative of the respiration of the subject, such as inspiration, expiration, or any combination, permutation, or component of the respiration of the subject. By measuring time intervals in association with one or more measured phases of respiration, this removes a source of variability of the time intervals due to patient respiration.

In some examples, the signal analyzer circuit 630 activates an alarm or alert to indicate the determined occurrence of an ischemic event. In some examples, the signal analyzer circuit 630 stores data associated with measured changes in intervals from the baseline time interval in memory. The signal analyzer circuit 630 can be configured to calculate trend data of the measured interval changes and to store the trend data in memory. In some examples, the signal analyzer circuit 630 uses the trend data of the time intervals to generate a heart failure status indication, such as to indicate a degree of heart failure that can be useful to track heart failure progression. In some examples, the IMD 305 transmits the trend data to an external device, such as for display to a local or remote user, or for transmission over a communication network.

In some examples, a baseline amplitude of at least one heart sound is normalized with respect to a measured amplitude of a second heart sound of the heart sound signal. Such normalization includes calculating a ratio between amplitudes of at least two different heart sounds associated with the same cardiac cycle. In some examples, a baseline amplitude of an S3 heart sound is normalized with respect to a measured amplitude of an S1 heart sound. In some examples, a baseline amplitude of an S4 heart sound is normalized with respect to a measured amplitude of an S3 heart sound. In some examples, a baseline amplitude of an S1, S3, and/or S4 heart sound is normalized with respect to a measured amplitude of an S2 heart sound.

In some examples, the signal analyzer circuit 630 is configured to measure a baseline amplitude of at least one heart sound of the heart sound signal normalized with respect to another measured characteristic of the heart sound signal. In some examples, the signal analyzer circuit 630 is configured to measure a baseline amplitude of at least one heart sound of the heart sound signal normalized with respect to one of a measured power of the heart sound signal measured during systole, a measured energy of the heart sound signal, and a measured are under a curve of the heart sound signal.

The signal analyzer circuit 630 determines that an ischemic event occurred, such as when it measures a specified change in the ratio from a ratio of the corresponding baseline amplitude (e.g., a percentage increase in the ratio from the corresponding baseline ratio), together with a measured change in a time interval from an established baseline time interval. The normalized amplitudes and the measured time intervals both give useful information about ischemia. Hence, a combination of the two may give better results.

Any combination of the intervals discussed previously with the normalized heart sounds discussed previously can be used to determine that an ischemic event occurred. For example, an ischemic event may be associated with both an increase in the amplitude of the S3 heart sound and a decrease of the S1 or S2 heart sound. The ischemic event may further be associated with a decrease in the S1-S2 time interval. The signal analyzer circuit 630 may determine that an ischemic event has occurred from a change in the S3 amplitude normalized with respect to S1 or S2, and the decrease in the S1-S2 time interval. In some examples, the signal analyzer circuit 630 uses one or more rules to combine the normalized amplitudes and the time intervals.

In some examples, the signal analyzer circuit 630 may use one or more rules to combine indications from one or more intervals, functions that include the intervals, or changes in normalized heart sound amplitudes. In one example, the signal analyzer circuit 630 may assign at least a first weight to the measured change from baseline in a time interval and may assign at least a second weight to a second sensed event such as a sensed normalized heart sound amplitude. The signal analyzer circuit 630 then declares an ischemic event to have occurred according to at least one rule incorporating the measured change in the time interval, the normalized amplitude, and the assigned weights. In some examples, the rule includes a decision matrix such as in Table 1.

Figure 9:
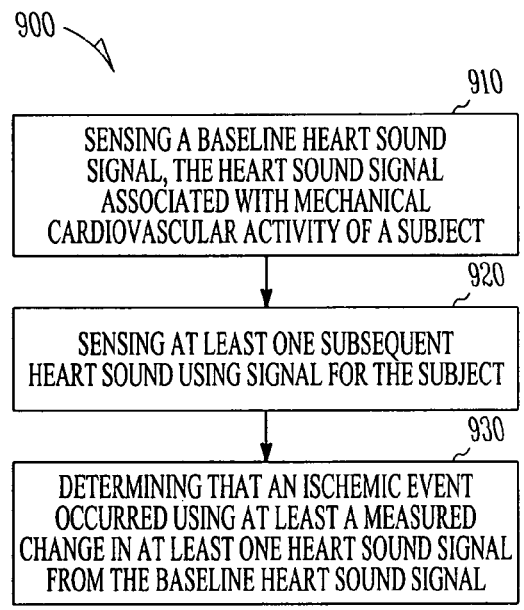
FIG. 9 is an example of a block diagram of a method of detecting ischemia using a heart sound sensor.

FIG. 9 is a block diagram of a method 900 of detecting ischemia using a heart sound sensor. At block 910, a baseline heart sound signal is sensed. The heart sound or sounds are associated with mechanical cardiovascular activity of a heart of a patient or subject. In some examples, a heart sound signal is sensed using an IMD. In some examples, the heart sound signal is sensed using an external device. In some examples, the heart sound signal is sensed using an IMD and a sampled version of the sensed signal is communicated to an external device for signal processing.

At block 920, at least one subsequent heart sound signal for the patient is sensed. In some examples, the baseline heart sound signal and subsequent heart sound signal are sensed in association with a posture of a patient, such as to reduce or remove the variability of the heart sound signal measurements with patient posture.

At block 930, an ischemic event is deemed to have occurred using at least a measured change in at least one heart sound from the corresponding baseline heart sound signal. In some examples, the heart sounds are continuously, or occasionally, monitored for changes from the corresponding baseline.

In some examples, an occurrence of an ischemic event is inferred from a specified measured increase in amplitude of a heart sound from a baseline heart sound amplitude. In some examples, the baseline includes sampled amplitudes stored in a memory. In some examples, the ischemic event is inferred using a specified measured decrease in amplitude of a heart sound from a baseline heart sound amplitude. In some examples, the ischemic event is inferred using a specified measured increase in amplitude of a first heart sound and a specified measured decrease in a second heart sound. In some examples, a normalization of a first heart sound with respect to a second heart sound is monitored. As an example, an occurrence of an ischemic event can be inferred from a specified increase in an S3/S1 amplitude ratio measured relative to a baseline value of the S3/S1 ratio. As another example, the ratio of the S4 amplitude to the S3 amplitude is monitored. An occurrence of an ischemic event can be inferred from a specified increase in an S4/S3 amplitude ratio measured relative to a baseline value of the S4/S3 ratio. In yet another example, the amplitude of the S1, S3, or S4 heart sound is normalized with respect to the S2 heart sound.

In some examples, an ischemic event can be deemed to have occurred by the appearance of a transient heart sound that is missing in the baseline heart sound signal. In certain examples, if the baseline heart sound signal has an absence of S3heart sounds, an ischemic event can be inferred when at least one transient S3 heart sound is detected in the signal. As another example, if the baseline heart sound signal has an absence of S4 heart sounds, an ischemic event can be inferred when at least one transient S4 heart sound is detected in the signal. In some examples, an ischemic event can be deemed to have occurred based on how often a heart sound missing in the baseline heart sound signal appears in the measured signal and then disappears. In some examples, an ischemic event can be deemed to have occurred based on how long the appearance of the previously-missing heart sound persists before it disappears. In some examples, an ischemic event can be inferred when a merging of S3 and S4 heart sounds is detected in the heart sound signal. In some examples, the merging may be heart rate related. An ischemic event can be inferred when the merging occurs at high heart rates when the time for diastole is shortened, such as at one hundred beats per minute (100 bpm) or higher.

In some examples, a signal power at one or more frequency components of one or more heart sounds is monitored, such as by monitoring a power spectrum of one or more heart sounds. A baseline of the power spectrum can be established for at least one heart sound, such as the S3 or S4 heart sound, such as by using a digital signal processing (DSP) fast Fourier transform (FFT). An occurrence of an ischemic event can be inferred from a specified measured change in the heart sound power spectrum from the corresponding baseline power spectrum. In some examples, a baseline for the entire heart sound sensor output is established over several cardiac cycles. An occurrence of an ischemic event can be inferred from a specified measured change in the heart sound sensor power spectrum from the corresponding baseline power spectrum.

In some examples, an occurrence of an ischemic event can be inferred from the amplitude of a heart sound normalized with respect to the power in that portion of the heart sound signal corresponding to the heart sound. In some examples, the method 900 further includes activating an alert or alarm to indicate that an ischemic event occurred. The alarm can include an audible or vibrating alarm from the IMD or a communication from the IMD to an external device that provides a visual, audible, or other alarm or alert either locally or remotely. The external device may receive an alarm status from the IMD when the IMD is next interrogated by the external device, or by a communication to the external device that is initiated by the IMD. The alarm may be used to notify the patient, a caregiver, or both a patient and caregiver of the ischemic event.

In some examples, an occurrence of an ischemic event can be inferred using both an intrinsic electrical cardiac signal sensed by the IMD and the measured change in the heart sound signal. In some examples, the occurrence of an ischemic event can be inferred when a specified measured change from established baselines occurs in both the cardiac signal and the heart sound signal. In some examples, an ischemic event can be inferred from timing relationships between the change or changes on the cardiac signal and the change or changes in the heart sound signal. In some examples, an ischemic event can be inferred using the temporal relationship of a sensed event indicated by the sensed cardiac signal and the specified measured change in the heart sound signal from the established baseline heart sound signal. As an illustrative example, an ischemic event can be inferred when the sensed event is no longer indicated by the sensed cardiac signal while the measured change in the heart sound signal continues to persist.

Figure 10:
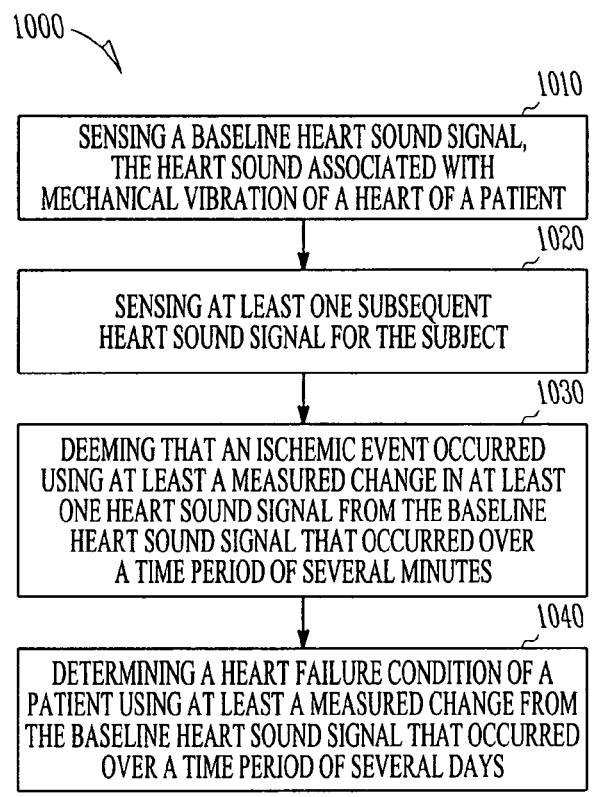
FIG. 10 is an example of a block diagram of an example of a method of detecting ischemia using a heart sound sensor.

FIG. 10 illustrates an example of a method 1000 of monitoring one or more mechanical functions of a heart. At block 1010, a baseline heart sound signal is sensed, and at block 1020, at least one subsequent heart sound signal for the patient is sensed using the IMD. At block 1030, an occurrence of an ischemic event can be inferred if a specified change in a heart sound signal from the corresponding baseline signal occurs within a specified acute time frame of several minutes (e.g., less than fifteen minutes). This is in contrast to a change that is detected by trending of heart sound signal measurements that indicate the change is occurring with a time constant of several hours or days (e.g., more than four hours). If the change from the baseline occurs over the course of hours or days, at block 1040, the method deems the change to indicate a worsening of a heart failure condition of the patient, rather than acute ischemia. In some examples, the method 1000 further includes activating a single alarm, regardless of the time frame of the detected change, or different alarms to distinguish between acute ischemia and heart failure.

Figure 11:
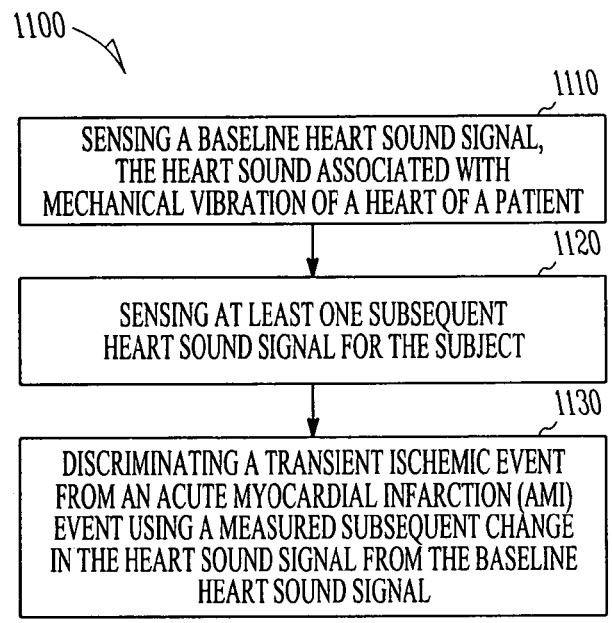
FIG. 11 is a block diagram of an example of a method of detecting ischemia using a heart sound sensor.

FIG. 11 illustrates another example of a method 1100 of monitoring one or more mechanical functions of a heart. At block 1110, a baseline heart sound signal is sensed, and at block 1120, at least one subsequent heart sound signal for the patient is sensed using the IMD. At block 1130, a transient ischemic event is discriminated from an AMI event, such as by using a measured subsequent change in the heart sound signal from the baseline heart sound signal. In some examples, transient ischemia is distinguished from AMI using an indication of how long the specified change in the heart sound persists. A longer duration indicates AMI, while a short duration indicates a transient event. In some examples, discriminating a transient ischemic event from an AMI event includes discriminating based on the measured amplitude of a subsequent change from the established baseline heart sound signal. A large amplitude change is likely to indicate an AMI event, while a small amplitude change is likely to indicate a transient ischemic event. In some examples, discriminating a transient ischemic event from an AMI event includes discriminating based on a temporal relationship of a sensed event indicated by a sensed cardiac signal and the measured subsequent change in the heart sound signal from the established baseline heart sound signal. An event indicated by both the cardiac signal change and the heart sound change is more likely to be an AMI event if the cardiac signal change goes away but the heart sound change remains. An event that is indicated by a cardiac signal change but occurs without a corresponding change in a heart sound signal is likely to be a transient ischemic change.

Figure 12:
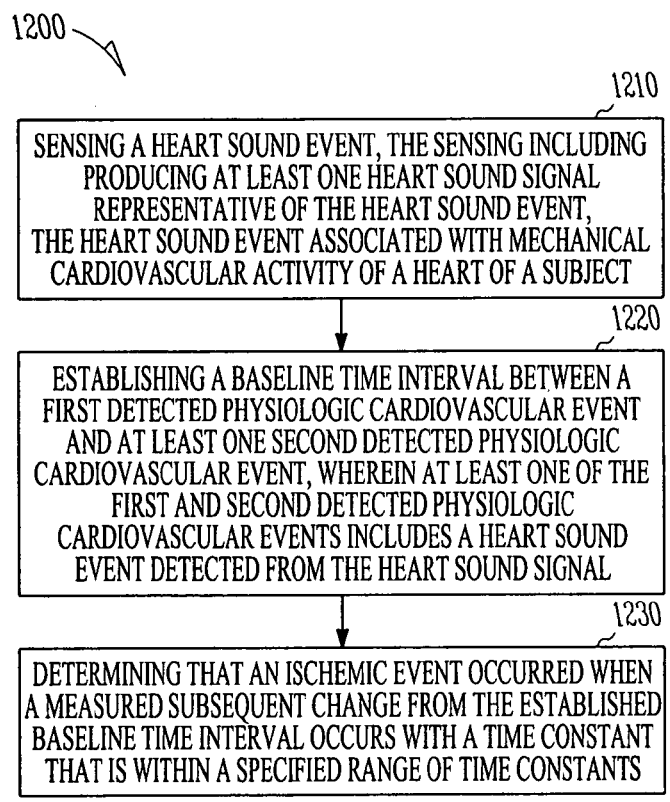
FIG. 12 is a block diagram of an example of a method of detecting ischemia using a heart sound sensor.

FIG. 12 illustrates another example of a method 1200 of monitoring one or more mechanical functions of a heart. At block 1210, a heart sound event is sensed. The sensing includes producing at least one heart sound signal representative of the heart sound event, the heart sound event is associated with mechanical cardiovascular activity of a heart of a subject. In some examples, the heart sound signal is produced using an external heart sound sensor. In some examples, the heart sound signal is produced using an implantable heart sound sensor. In some examples, the heart sound signal is produced using an implantable heart sound sensor and a sampled version of the signal is communicated to an external device for processing.

At block 1220, a baseline time interval is established between a first detected physiologic cardiovascular event and at least one second detected physiologic cardiovascular event, wherein at least one of the first and second detected physiologic cardiovascular events includes a heart sound event detected from the heart sound signal.

At block 1230, an ischemic event is determined to have occurred when a measured subsequent change from the established baseline time interval occurs with a time constant that is within a specified range of time constants. For example, assume a running average is used to measure a baseline time interval. An episode may be determined to be an ischemic event if the measured change from the baseline time interval occurs relatively suddenly with a time constant that ranges from a few seconds to a few minutes (e.g., five minutes) from the last value used for the running average. In some examples, the measured change in an interval must exceed a specified threshold change within the specified time duration. In some examples, once it is determined that either an ischemic event occurred or that a condition of HF is worsening, the method 1200 includes re-establishing a baseline time interval some time after the event.

In some examples, determining the baseline time interval includes determining a baseline time interval from a sensed R-wave of a QRS complex to a heart sound event. In this example, the heart sound event may include the S1 heart sound or the S2 heart sound, and the interval may be the R-S1 interval or the R-S2 interval. In some examples, determining the baseline time interval includes determining a baseline time interval from a sensed Q-wave of a QRS complex to a heart sound event. In this example, the heart sound event may include the S1 heart sound or the S2 heart sound, and the interval may be the Q-S1 interval or the Q-S2 interval.

In some examples, both the first and second detected physiologic cardiovascular event include a heart sound event. Determining the baseline time interval may include determining a baseline time interval from one or more of an S1 heart sound to an S2 heart sound (S1-S2), a time interval from an S2 heart sound to an S3 heart sound (S2-S3), a time interval from an S4 heart sound to an S1 heart sound (S4-S1), a time interval from an S2 heart sound to an S4 heart sound (S2-S4), a time interval from an aortic component of an S1 heart sound to an aortic component of an S2 heart sound, a time interval from a mitral component of an S1 heart sound to an aortic component of the S1 heart sound, and a time interval from an aortic component of an S2 heart sound to a pulmonary component of the S2 heart sound.

In some examples, the method 1200 includes measuring a baseline amplitude of at least one heart sound in association with a signal from at least one second sensor. The second sensor signal is representative of a physiologic condition of the subject. In some examples, the second sensor is a posture sensor and the heart sound signal is measured in association with one or more postures of a subject. In some examples, the second sensor is an activity sensor and the heart sound signal is measured in association with activity of a subject. In some examples, the second sensor is a respiration sensor and the heart sound signal is measured in association with one or more phases of respiration of a subject.

In some examples, the method 1200 includes measuring a baseline amplitude of at least one heart sound normalized with respect to a measured characteristic of the heart sound signal. In some examples, a baseline amplitude of at least one heart sound is normalized with respect to one of a measured amplitude of a second heart sound of the heart sound signal, a measured power of the heart sound signal measured during systole, a measured energy of the heart sound signal, and a measured area under a curve of the heart sound signal.

In some examples, a baseline amplitude of an S3 heart sound is normalized with respect to a measured amplitude of an S1 heart sound. In some examples, a baseline amplitude of an S4 heart sound is normalized with respect to a measured amplitude of an S3 heart sound. In some examples, a baseline amplitude of an S1, S3, and/or S4 heart sound is normalized with respect to a measured amplitude of an S2 heart sound.

An occurrence of an ischemic event is determined using a specified measured subsequent change from the established baseline time interval and a specified measured subsequent change from the baseline normalized amplitude. For example, an ischemic event may be associated with both an increase in the amplitude of the S3 heart sound and a decrease in the amplitude of the S1 or S2 heart sound. The ischemic event may further be associated with a decrease in the S2-S3 time interval. A device may determine that an ischemic event occurred using a specified measured subsequent change S2-S3 interval from its established baseline value, and a specified measured subsequent change of the S3 amplitude, normalized using the S1 or S2 amplitude, from the established baseline value of such normalization.

Figure 13:
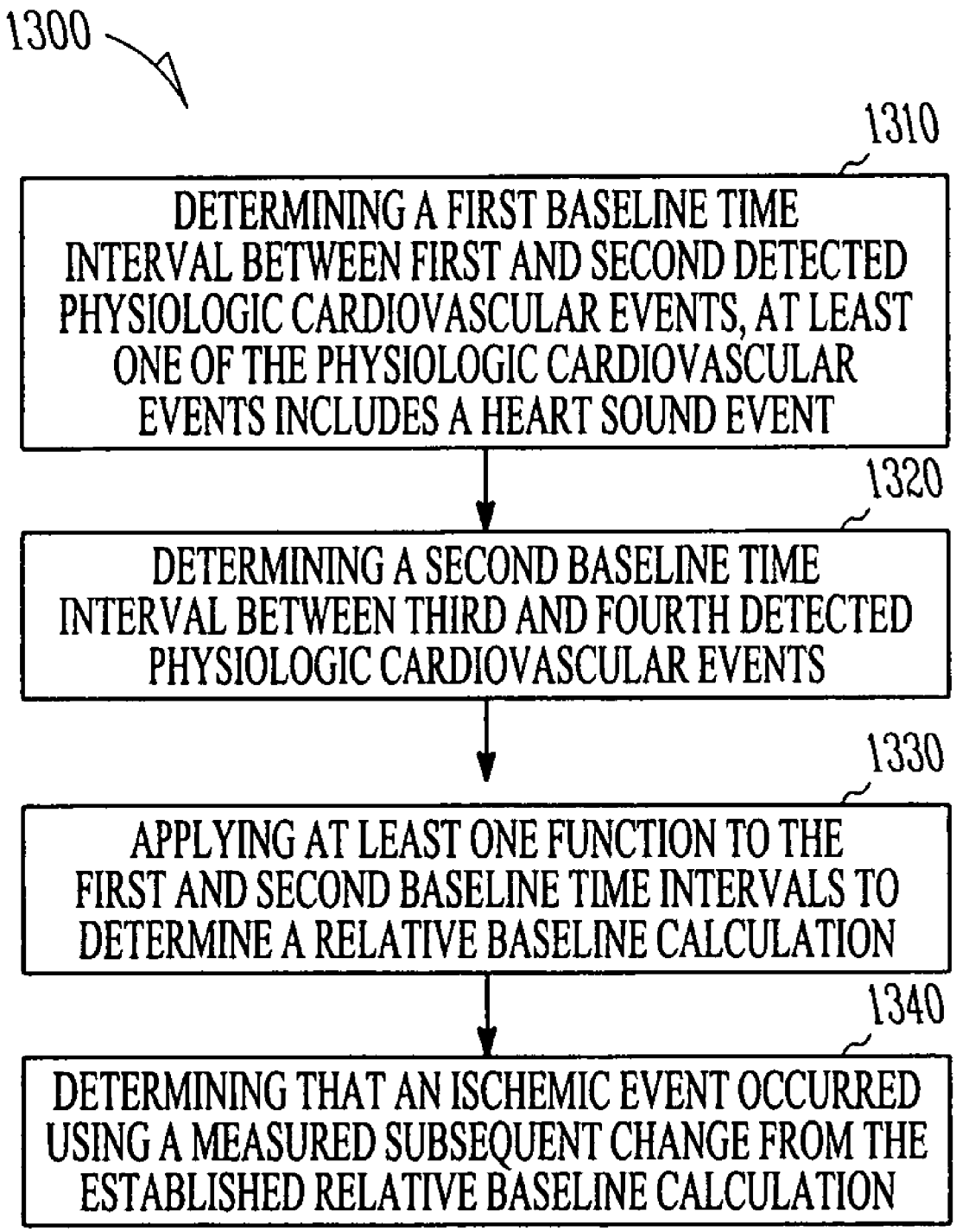
FIG. 13 is a block diagram of an example of a method of detecting ischemia using a heart sound sensor.

FIG. 13 illustrates another example of a method 1300 of monitoring one or more mechanical functions of a heart. At block 1310, a first baseline time interval is determined between first and second events, such as a first detected physiologic cardiovascular event and a second detected physiologic cardiovascular event. At least one of the first and second physiologic events includes a first heart sound event detected from a heart sound signal. At block 1320, at least a second baseline time interval is determined between a third detected physiologic cardiovascular event and a fourth detected physiologic cardiovascular event.

At block 1330, at least one function is applied to the first and second baseline time intervals, such as to determine a relative baseline calculation. The function can be any function applied to the first and second baseline time intervals, such as a ratio of the first and second baseline time intervals, for example. At block 1350, an ischemic event can be inferred upon detection of a measured subsequent change of the relative function of the first and second time intervals from its baseline value. In some examples, an ischemic event can be inferred from a measured subsequent change in the output of the function of the first and second time intervals that is different from the established baseline calculation by at least a specified threshold change value.

In some examples, the first time interval includes an interval from a sensed R-wave of a QRS complex to a sensed S1 heart sound (R-S1) during the same cardiac cycle, and the second time interval includes an interval from the S1 heart sound to an S2 heart sound. In this example, the function includes a ratio including the first interval and the second interval [e.g., (R-S1)/(S1-S2), or (S1-S2)/(R-S1)]. The IMD may determine that an ischemic event occurred from a specified detected increase in the (R-S1)/(S1-S2) ratio from an established baseline value of the ratio for example.

In some examples, In some examples, the first time interval includes an interval from a sensed R-wave to a sensed S1 heart sound (R-S1) during the same cardiac cycle, and the second interval is a time duration between cardiac cycles, such as an R-wave to R-wave interval (R-R). In this example, the function includes a ratio including the first interval and the second interval [e.g., (R-S1)/(R-R), or (R-R)/(R-S1)]. The IMD may determine that an ischemic event occurred from a specified detected increase in the (R-S1)/(R-R) ratio from a baseline value of the ratio for example.

In some examples, the first time interval includes an interval from a sensed Q-wave of a QRS complex to a sensed S1 heart sound (Q-S1), and the second time interval includes an interval from the S1 heart sound to an S2 heart sound from. In this example, the function includes a ratio including the first interval and the second interval [e.g., (Q-S1)/(S1-S2), or (Q-S1)/S1-S2)]. The IMD may determine that an ischemic event occurred from detecting a specified increase in the (Q-S1)/(S1-S2) ratio from an established baseline value of the ratio for example.

In some examples, the first time interval includes an interval from a sensed Q-wave of a QRS complex to an S1 heart sound (Q-S1). The second time interval includes a time interval from an S2 heart sound to an S3 heart sound (S2-S3), and the function includes a ratio including the first time interval and the second time interval [e.g., (S2-S3)/(Q-S1), or (Q-S1)/(S2-S3)]. The IMD may determine that an ischemic event occurred from detecting a specified decrease in the (S2-S3)/(Q-S1) ratio from an established baseline value of the ratio for example.

In some examples, the first time interval includes an interval between S1 and S2 heart sounds of the same cardiac cycle "A" ($S1_A$-$S2_A$), and the second time interval includes an interval between the same S2 heart sound and the S1 heart sound of the subsequent cardiac cycle "B" ($S2_A$-$S1_B$). The function includes a ratio including the first time interval and the second time interval [e.g., ($S1_A$-$S2_A$)/($S2_A$-$S1_B$), or ($S2_A$-$S1_B$)/($S1_A$-$S2_A$)]. The IMD may determine that an ischemic event occurred from detecting a specified increase in the ($S1_A$-$S2_A$)/($S2_A$-$S1_B$) ratio from a baseline value of the ratio for example.

In some examples, the first time interval includes an interval between a Q-wave and S2 heart sound of the same cardiac cycle ($Q_A$-$S2_A$), and the second time interval includes an interval between the same S2 heart sound and the Q-wave of the subsequent cardiac cycle ($S2_A$-$Q_B$). The function includes a ratio including the first time interval and the second time interval [e.g., ($Q_A$-$S2_A$)/($S2_A$-$Q_B$), or ($S2_A$-$Q_B$)/($Q_A$-$S2_A$)]. The IMD may determine that an ischemic event occurred from detecting a specified increase in the ($Q_A$-$S2_A$)/($S2_A$-$Q_B$) ratio from a baseline value of the ratio for example.

In some examples, the first time interval includes an interval from a sensed S2 heart sound to a sensed S3 heart sound, and the second time interval includes a time interval from the S2 heart sound to a sensed S4 heart sound. In this example, the function includes a ratio including the first interval and the second interval [e.g., (S2-S3)/(S2-S4), or (S2-S4)/S2-S3)]. The IMD may determine that an ischemic event occurred from detecting a specified decrease in the (S2-S3)/(S2-S4) ratio from an established baseline value of the ratio. In some examples, one or more rules are used to combine indications from one or more intervals, functions that include the intervals, or changes in normalized heart sound amplitudes.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72(b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A device comprising:
a heart sound sensor configured to produce a heart sound signal representative of a heart sound, the heart sound associated with mechanical cardiovascular activity of a heart of a subject; and
a signal analyzer circuit in electrical communication with the heart sound sensor, wherein the signal analyzer circuit is configured to:
establish a baseline value of a time interval between a first detected physiologic cardiovascular event and at least one second detected physiologic cardiovascular event, wherein the first and second detected events occur during a same cardiac cycle, wherein at least one of the first and second detected physiologic cardiovascular events includes a heart sound event detected using the heart sound signal, and wherein the other of the first and second detected physiologic cardiovascular events is associated with a different event;
after establishing the baseline, then monitor the time interval over a plurality of cardiac cycles; and
determine that an ischemic event occurred using information about how quickly a specified change from the established baseline time interval value occurs during the monitored plurality of cardiac cycles.

2. The device of claim 1, further including at least one cardiac signal sensing circuit coupled to the signal analyzer circuit, the cardiac signal sensing circuit configured to produce an electrical cardiac signal representative of cardiac activity of the subject, wherein the first detected physiologic cardiovascular event includes a sensed Q-wave of a QRS complex.

3. The device of claim 2, wherein the second detected physiologic cardiovascular event includes a heart sound selected from the group consisting of:
an S1 heart sound; and
an S2 heart sound.

4. The device of claim 1, further including at least one cardiac signal sensing circuit coupled to the signal analyzer circuit, the cardiac signal sensing circuit configured to produce an electrical cardiac signal representative of cardiac activity of the subject, wherein the first detected physiologic cardiovascular event includes a sensed R-wave of a QRS complex.

5. The device of claim 1, wherein the first detected physiologic cardiovascular event includes a first heart sound and the second detected physiologic cardiovascular event includes a second heart sound.

6. The device of claim 1, wherein the time interval between the first detected physiologic cardiovascular event and the second detected physiologic cardiovascular event includes a time interval selected from the group consisting of:
a time interval from an S1 heart sound to an S2 heart sound;
a time interval from an S2 heart sound to an S3 heart sound;
a time interval from an S4 heart sound to an S1 heart sound;
a time interval from an S2 heart sound to an S1 heart sound; and
a time interval from an aortic component of an S1 heart sound to an aortic component of an S2 heart sound.

7. The device of claim 1, wherein the signal analyzer circuit is further configured to measure:
a first baseline time interval between the first and second detected physiologic cardiovascular events, wherein at least one of the first and second detected physiologic cardiovascular events includes a first detected heart sound event;
at least a second baseline time interval between third and fourth detected physiologic cardiovascular events; and
wherein the signal analyzer circuit is configured to apply at least one function to the first and second baseline time intervals to determine a relative baseline calculation and to determine that an ischemic event occurred using a measured subsequent change from the established relative baseline calculation.

8. The device of claim 7, including at least one cardiac signal sensing circuit coupled to the signal analyzer circuit, the cardiac signal sensing circuit configured to produce an electrical cardiac signal representative of cardiac activity of the subject, and wherein the first detected physiologic cardiovascular event includes a sensed Q-wave (Q) of a QRS complex.

9. The device of claim 8, wherein the first detected heart sound event is an S1 heart sound, wherein the third and fourth detected physiologic cardiovascular events are the S1 heart sound and an S2 heart sound respectively, and wherein the function includes a ratio including the first interval and the second interval.

10. The device of claim 8, wherein the first detected heart sound event is an S1 heart sound, wherein third and fourth detected physiologic cardiovascular events are S2 and S3 heart sounds respectively, and wherein the function includes a ratio including the first interval and the second interval.

11. The device of claim 7, wherein the first detected physiologic cardiovascular event includes the S2 heart sound, wherein the second detected physiologic cardiovascular event includes an S3 heart sound, wherein the third and fourth detected physiologic cardiovascular events are S2 and S4 heart sounds respectively, and wherein the function includes a ratio including the first interval and the second interval.

12. The device of claim 7, including at least one cardiac signal sensing circuit coupled to the signal analyzer circuit, the cardiac signal sensing circuit configured to produce an electrical cardiac signal representative of cardiac activity of the subject, wherein the first detected physiologic cardiovascular event includes a sensed R-wave (R) of a QRS complex, wherein the first detected heart sound event is an S1 heart sound, wherein the third and fourth detected physiologic cardiovascular events are the S1 heart sound and an S2 heart sound respectively, and wherein the function includes a ratio including the first interval and the second interval.

13. The device of claim 1, wherein the signal analyzer circuit is further configured to:

measure a baseline amplitude of a first heart sound of the heart sound signal normalized with respect to a measured characteristic of the heart sound signal; and determine that an ischemic event occurred using a measured change in a time interval from the established baseline time interval and a measured change in a normalized amplitude from an established baseline normalized amplitude.

14. The device of claim 13, wherein the measured characteristic of the heart sound signal is selected from the group consisting of:

a measured amplitude of a second heart sound of the heart sound signal;

a measured power of the heart sound signal measured during systole;

a measured energy of the heart sound signal; and a measured area under a curve of the heart sound signal.

15. The device of claim 13, wherein the first heart sound of the heart sound signal normalized with respect to a measured characteristic of the heart sound signal includes at least one of:

an S3 heart sound amplitude normalized with respect to an S1 heart sound amplitude;

an S4 heart sound amplitude normalized with respect to an S3 heart sound amplitude;

an S1 heart sound amplitude normalized with respect to an S2 heart sound amplitude;

an S3 heart sound amplitude normalized with respect to an S2 heart sound amplitude; and an S4 heart sound amplitude normalized with respect to an S2 heart sound amplitude.

16. The device of claim 1, further including at least one second sensor in electrical communication with the signal analyzer circuit, the second sensor configured to produce a second sensor signal representative of a physiologic condition of a subject; and wherein the signal analyzer circuit is configured to measure a heart sound in association with the second sensor signal.

17. The device of claim 16, wherein the second sensor includes at least one sensor selected from the group consisting of:

a posture sensor, and the signal analyzer circuit configured to measure a heart sound in association with posture of the subject;

an activity sensor, and the signal analyzer circuit configured to measure a heart sound in association with activity of the subject; and a respiration sensor, and the signal analyzer circuit configured to measure a heart sound in association with respiration of the subject.

18. The device of claim 1, wherein the signal analyzer circuit is further configured to re-establish a baseline heart sound signal if the signal analyzer circuit determines an ischemic event has occurred.

19. The device of claim 1, wherein the signal analyzer circuit is further configured to:

distinguish between an ischemic event that occurred and a heart failure condition that has worsened by using a time constant of the measured subsequent change from the baseline signal; and to re-establish a baseline heart sound signal if the signal analyzer circuit determines a heart failure condition has worsened.

20. A method comprising:

sensing a heart sound event using a heart sound sensor, the sensing including producing at least one heart sound signal representative of the heart sound event, the heart sound event associated with mechanical cardiovascular activity of a heart of a subject;

using a signal analyzer circuit in communication with the heart sound sensor, establishing a baseline time interval between a first detected physiologic cardiovascular event and at least one second detected physiologic cardiovascular event, wherein the first and second detected physiologic cardiovascular events occur during a same cardiac cycle, wherein at least one of the first and second detected physiologic cardiovascular events includes a heart sound event detected using the heart sound signal, and wherein the other of the first and second detected physiologic cardiovascular events is associated with a different event;

after establishing the baseline, then monitoring the time interval over a plurality of cardiac cycles; and determining, using the signal analyzer circuit, that an ischemic event occurred using information about how quickly a specified change from the established baseline time interval value occurs during the monitored plurality of cardiac cycles.

21. The method of claim 20, wherein determining the baseline time interval includes determining a baseline time interval from a sensed Q-wave of a QRS complex to a heart sound event.

22. The method of claim 21, wherein determining the baseline time interval includes determining a baseline time interval from a sensed Q-wave of a QRS complex to at least one of:

an S1 heart sound; and an S2 heart sound.

23. The method of claim 20, wherein determining the baseline time interval includes determining a baseline time interval from a sensed R-wave of a QRS complex to a heart sound event.

24. The method of claim 20, wherein determining the baseline time interval determining at least one interval from the group of time intervals consisting of:

a time interval from an S1 heart sound to an S2 heart sound;

a time interval from an S2 heart sound to an S3 heart sound;

a time interval from an S4 heart sound to an S1 heart sound;

a time interval from an S2 heart sound to an S4 heart sound; and a time interval from an aortic component of an S1 heart sound to an aortic component of an S2 heart sound.

25. The method of claim 20, wherein the baseline time interval is a first baseline time interval, and wherein the method further includes:

determining at least a second baseline time interval between third and fourth detected physiologic cardiovascular events;

applying at least one function to the first and second baseline time intervals to determine a relative baseline calculation; and determining that an ischemic event occurred using a measured subsequent change from the established relative baseline calculation.

26. The method of claim 25, wherein the first baseline time interval includes a time interval from a sensed Q-wave of a QRS complex to an S1 heart sound, wherein the second baseline time interval includes a time interval from the S1 heart sound to and an S2 heart sound, and wherein the function includes a ratio including the first interval and the second interval.

27. The method of claim 25, wherein the first baseline time interval includes a time interval from a sensed Q-wave of a QRS complex to an S1 heart sound, wherein the second baseline time interval includes a time interval from an S2 heart sound to an S3 heart sound, and wherein the function includes a ratio including the first interval and the second interval.

28. The method of claim 25, wherein the first baseline time interval includes a time interval from an S2 heart sound to an S3 heart sound, wherein the second baseline time interval includes a time interval from an S2 heart sound to an S4 heart sound, and wherein the function includes a ratio including the first interval and the second interval.

29. The method of claim 25, wherein the first baseline time interval includes a time interval from a sensed R-wave of a QRS complex to an S1 heart sound, wherein the second baseline time interval includes a time interval from the S1 heart sound to and an S2 heart sound, and wherein the function includes a ratio including the first interval and the second interval.

30. The method of claim 20, further including:
measuring a baseline amplitude of at least one heart sound of a heart sound signal normalized with respect to a measured characteristic of the heart sound signal; and
determining that an ischemic event occurred using a measured change in an interval from the established baseline time interval and a measured change in the normalized amplitude from an established baseline normalized amplitude.

31. The method of claim 30, wherein measuring a baseline amplitude includes measuring a characteristic of the heart sound signal selected from the group consisting of:
a measured amplitude of a second heart sound of the heart sound signal;
a measured power of the heart sound signal measured during systole;
a measured energy of the heart sound signal; and
a measured area under a curve of the heart sound signal.

32. The method of claim 30, wherein measuring a baseline amplitude of at least one heart sound of a heart sound signal normalized with respect to a measured characteristic of the heart sound signal includes measuring at least one of:
an S3 heart sound amplitude normalized with respect to an S1 heart sound amplitude;
an S4 heart sound amplitude normalized with respect to an S3 heart sound amplitude;
an S1 heart sound amplitude normalized with respect to an S2 heart sound amplitude;
an S3 heart sound amplitude normalized with respect to an S2 heart sound amplitude; and
an S4 heart sound amplitude normalized with respect to an S2 heart sound amplitude.

33. The method of claim 20, further including producing at least one second sensor signal representative of a physiologic condition of the subject, and wherein sensing a heart sound event includes sensing the heart sound event in association with the second sensor signal.

34. The method of claim 33, sensing the heart sound event in association with the second sensor signal includes sensing at least one of:
sensing the heart sound event in association with a posture signal indicative of a posture of the subject;
sensing the heart sound event in association with an activity signal indicative of activity of the subject; and
sensing the heart sound event in association with a respiration signal representative of a respiration of the subject.

35. The method of claim 20, further including re-establishing a baseline heart sound signal if the signal analyzer circuit determines an ischemic event has occurred.

36. The method of claim 20, further including:
distinguishing between an ischemic event that occurred and a heart failure condition that has worsened by using a time constant of the measured subsequent change from the baseline signal; and
re-establishing a baseline heart sound signal if the signal analyzer circuit determines a heart failure condition has worsened.

* * * * *